US011638744B2

(12) United States Patent
Shibayama et al.

(10) Patent No.: US 11,638,744 B2
(45) Date of Patent: May 2, 2023

(54) IMMUNITY ENHANCING AGENT FOR CANCER BY ALLERGIN-1 ANTAGONIST

(71) Applicant: ONO PHARMACEUTICAL CO., LTD., Osaka (JP)

(72) Inventors: Shiro Shibayama, Ibaraki (JP); Hiroshi Arima, Ibaraki (JP); Takuya Simbo, Ibaraki (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/757,452

(22) PCT Filed: Sep. 2, 2016

(86) PCT No.: PCT/JP2016/075887
§ 371 (c)(1),
(2) Date: Mar. 5, 2018

(87) PCT Pub. No.: WO2017/038997
PCT Pub. Date: Mar. 9, 2017

(65) Prior Publication Data
US 2018/0244771 A1   Aug. 30, 2018

(30) Foreign Application Priority Data

Sep. 3, 2015  (JP) .............. JP2015-173659
Jul. 13, 2016  (JP) .............. JP2016-138374

(51) Int. Cl.
| *A61K 38/17* | (2006.01) |
| *C07K 14/705* | (2006.01) |
| *A61K 45/06* | (2006.01) |
| *A61K 38/00* | (2006.01) |
| *A61K 45/00* | (2006.01) |
| *A01K 67/027* | (2006.01) |
| *A61P 35/02* | (2006.01) |
| *C07K 16/28* | (2006.01) |
| *A61K 39/00* | (2006.01) |
| *A61K 39/395* | (2006.01) |

(52) U.S. Cl.
CPC ........ *A61K 38/177* (2013.01); *A01K 67/0276* (2013.01); *A61K 38/00* (2013.01); *A61K 45/00* (2013.01); *A61K 45/06* (2013.01); *A61P 35/02* (2018.01); *C07K 16/283* (2013.01); *A01K 2207/12* (2013.01); *A01K 2217/075* (2013.01); *A01K 2227/105* (2013.01); *A01K 2267/0331* (2013.01); *A61K 39/3955* (2013.01); *A61K 2039/505* (2013.01); *A61K 2300/00* (2013.01); *C07K 16/2812* (2013.01); *C07K 16/2818* (2013.01); *C07K 2319/75* (2013.01)

(58) Field of Classification Search
CPC .............. C07K 2319/30; C07K 2319/32
See application file for complete search history.

(56) References Cited

U.S. PATENT DOCUMENTS

| 6,348,574 B1* | 2/2002 | Godiska .............. C07K 14/705 |
| | | 530/350 |
| 7,595,048 B2 | 9/2009 | Honjo et al. |
| 7,910,697 B2 | 3/2011 | Odani et al. |
| 8,008,449 B2 | 8/2011 | Korman et al. |
| 2003/0044901 A1* | 3/2003 | Coleman .............. C07K 14/705 |
| | | 435/69.1 |
| 2003/0232411 A1 | 12/2003 | Fukushima et al. |
| 2008/0020990 A1* | 1/2008 | Yano .................. A61K 31/7105 |
| | | 514/44 A |
| 2009/0306349 A1* | 12/2009 | Hutchins ............ C07K 16/2863 |
| | | 530/391.1 |
| 2011/0165184 A1 | 7/2011 | Nishimura et al. |
| 2013/0022614 A1* | 1/2013 | Penichet ............ C07K 16/3069 |
| | | 424/156.1 |
| 2015/0005361 A1* | 1/2015 | Slukvin .............. G01N 33/5044 |
| | | 514/44 A |
| 2016/0272708 A1* | 9/2016 | Chen .................. C07K 16/2818 |
| 2016/0289315 A1* | 10/2016 | Mirza .................... C07K 16/22 |

FOREIGN PATENT DOCUMENTS

| JP | 2006-340714 A | 12/2006 |
| KR | 10-2012-0082255 A | 7/2012 |
| RU | 2483078 C2 | 5/2013 |
| WO | 0114424 A2 | 3/2001 |
| WO | 2006/121168 A1 | 11/2006 |
| WO | 2007005874 A2 | 1/2007 |
| WO | 2007/122815 A1 | 11/2007 |
| WO | 2008156712 A1 | 12/2008 |

OTHER PUBLICATIONS

Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Harris (Biotechnology, vol. 11, p. 1293-1297, 1993) (Year: 1993).*
Colman P. M. (Research in Immunology, 145:33-36, 1994) (Year: 1994).*
Gao et al. (The AAPS Journal, 2007, 9:E92-E104) (Year: 2007).*
Parker et al (Expert Reviews in Molecular Medicine, 2003, 5:1-15) (Year: 2003).*
Verma and Somia (Nature, 1997, 389:239-242) (Year: 1997).*
McNaughton (Proceedings of the National Academy of Sciences, USA, vol. 106, No. 15, p. 6111-6116, 2009) (Year: 2009).*
Eck and Wilson (Goodman & Gilman's The Pharmacological basis of Therapeutics, 1996, McGraw-Hill, New York, NY. p. 77-101) (Year: 1996).*
Niidome and Huang (Gene Therapy, 2002, 9:1647-1652) (Year: 2002).*

(Continued)

*Primary Examiner* — Michael Allen
(74) *Attorney, Agent, or Firm* — Sughrue Mion, PLLC

(57) ABSTRACT

A method for suppression of progress of, suppression of recurrence of and/or treatment of cancer, by administering an Allergin-1 antagonist in a therapy of a cancer patient with insufficient therapeutic efficacy by a tumor immunotherapeutic agent, or a cancer therapy in combination with an anti-cancer drug.

18 Claims, 14 Drawing Sheets

Specification includes a Sequence Listing.

(56) References Cited

OTHER PUBLICATIONS

Zhang et al (Molecular Therapy, 2012, 20:1298-1304) (Year: 2012).*
Rudikoff et al. (Proceedings of the National Academy of Sciences USA, vol. 79, p. 1979-1983, 1982) (Year: 1982).*
Huang (The Journal of Biological Chemistry, vol. 272, No. 43, p. 27155-27159, 1997) (Year: 1997).*
Martindale (Nature Genetics, vol. 18, p. 150-154, 1998) (Year: 1998).*
Nonaka (Human Molecular Genetics, vol. 18, No. 18, p. 3353-3364, 2009) (Year: 2009).*
Mendoza (Arch. Immunol. Ther. Exp., vol. 53, p. 47-60, 2005) (Year: 2005).*
Communication dated Apr. 27, 2018, from the National Office of Intellectual Property of Vietnamese in counterpart application No. 1-2018-00890.
Mahoney, et al., "Combination cancer immunotherapy and new immunomodulatory targets", 2015, Nature Reviews, vol. 14, Issue No. 8, pp. 561-584, XP 055240365.
Communication dated Feb. 11, 2019, issued by the European Patent Office in counterpart European Patent Application No. 16842026.3.
Communication dated May 8, 2019, from the Intellectual Property Office of Singapore in counterpart Application No. 11201801699V.
"APC anti-mouse Allergin-1 Antibody" BioLegend, Nov. 30, 2012 [retrieved from https://www.biolegend.com/en-us/products/apc-anti-mouse-allergin-1-antibody-8028 ] (4 pages total).
Rimas J. Orentas et al. "Identification of cell surface proteins as potential immunotherapy targets in 12 pediatric cancers" Frontiers in Oncology, Dec. 17, 2012, [retrieved from https://www.frontiersin.org/articles/10.3389/fonc.2012.00194/full ] (22 pages total).
Nagai Kei et al., Allergy & Immunology, vol. 18, No. 4, (2011), (pp. 506-514).
Satoko Tahara-Hanaoka et al., "An Immunoglobulin-Like Receptor, Allergin-1 Regulates the Activation of Mast Cells", Arerugi. 62(11), (2013), (pp. 1451-1457).
Satoshi Ueha et al., "Robust Antitumor Effects of Combined Anti-CD4-Depleting Antibody and Anti-PD-1/PD-L1 Immune Checkpoint Antibody Treatment in Mice", Research Article, Cancer Immunology Research, 2015, (2015), (pp. 631-640, 11 Pages Total).
Akira Shibuya et al., "Inhibitory Immunoreceptors on Mast Cells in Allergy and Inflammation", Innovative Medicine, Innovative Medicine, (2015), (pp. 95-107).
Satoshi Tsurusaki et al., "Allergin-1 inhibits TLR2-mediated mast cell activation and suppresses dermatitis", International Immunology, vol. 28, No. 12, The Japanese Society for Immunology, (2016), (pp. 605-609).
Kentaro Nanatsue et al., "Influence of MILR1 promoter polymorphism on expression levels and the phenotype of atopy", Original Article, The Japan Society of Human Genetics, Journal of Human Genetics (2014), (pp. 1-4).
Kaori Hitomi et al., "An immunoglobulin-like receptor, Allergin-1, inhibits immunoglobulin E-mediated immediate hypersensitivity reactions", Nature Immunology, vol. 11, No. 7, Nature America, Inc, (Jul. 2010), (pp. 601-608, 8 Pages Total).
Kei Nagai et al., "Expression and Function of Allergin-1 on Human Primary Mast Cells", vol. 8, Issue 10, PLOS One, e76160, (Oct. 2013), (8 Pages Total).
Satoko Tahara.,"An immunoglobulin-like receptor, Allergin-1", Journal of Clinical and Experimental Medicine, vol. 245, No. 3, Ishiyaku Pub.,Inc., (2013), (7 Pages Total).
Tatsuhiko Kodama., vol. 43 "Hirogaru 'Cha no. Shizuku Sekken' Higai", Journal of Clinical and Experimental Medicine, vol. 240, No. 4, (2012), (7 Pages Total).
Communication dated Feb. 21.2017, from the Japanese Patent Office in counterpart application No. 2017-503028.
International Search Report, issued by International Searching Authority in corresponding International Application No. PCT/JP2016/075887, dated Oct. 4, 2016, (PCT/ISA/210).
Written Opinion, issued by International Searching Authority in corresponding International Application No. PCT/JP2016/075887, dated Oct. 4, 2016, (PCT/ISA/237).
Communication dated Feb. 21, 2020, issued by the Russian Patent Office in Russian Application No. 2018107687/04.
The State Intellectual Property Office of P R. China, Communication dated Dec. 2, 2020 issued in counterpart Chinese Application No. 201680050962.5.
Communication dated Jul. 1, 2020 issued by the Intellectual Property Office of Singapore in counterpart Application No. 11201801699.
Office Action dated Jul. 5, 2021, issued by the State Intellectual Property Office of P.R. China in English counterpart Chinese Patent Application No. 201680050962.5 Translation.
Office Action dated Feb. 21, 2022 by the Intellectual Property Office of India in counterpart Indian English Patent Application No. 201847007882.

* cited by examiner

SEQUENCE LISTING

<160> NUMBER OF SEQ ID NOS: 8

<210> SEQ ID NO 1
<211> LENGTH: 343
<212> TYPE: PRT
<213> ORGANISM: Homo sapiens

<400> SEQUENCE: 1

```
Met Trp Ser His Leu Asn Arg Leu Leu Phe Trp Ser Ile Phe Ser Ser
1               5                   10                  15

Val Thr Cys Arg Lys Ala Val Leu Asp Cys Glu Ala Met Lys Thr Asn
            20                  25                  30

Glu Phe Pro Ser Pro Cys Leu Asp Ser Lys Thr Lys Val Val Met Lys
        35                  40                  45

Gly Gln Asn Val Ser Met Phe Cys Ser His Lys Asn Lys Ser Leu Gln
    50                  55                  60

Ile Thr Tyr Ser Leu Phe Arg Arg Lys Thr His Leu Gly Thr Gln Asp
65                  70                  75                  80

Gly Lys Gly Glu Pro Ala Ile Phe Asn Leu Ser Ile Thr Glu Ala His
                85                  90                  95
```

```
Glu Ser Gly Pro Tyr Lys Cys Lys Ala Gln Val Thr Ser Cys Ser Lys
            100                 105                 110

Tyr Ser Arg Asp Phe Ser Phe Thr Ile Val Asp Pro Val Thr Ser Pro
        115                 120                 125

Val Leu Asn Ile Met Val Ile Gln Thr Glu Thr Asp Arg His Ile Thr
130                 135                 140

Leu His Cys Leu Ser Val Asn Gly Ser Leu Pro Ile Asn Tyr Thr Phe
145                 150                 155                 160

Phe Glu Asn His Val Ala Ile Ser Pro Ala Ile Ser Lys Tyr Asp Arg
                165                 170                 175

Glu Pro Ala Glu Phe Asn Leu Thr Lys Lys Asn Pro Gly Glu Glu Glu
        180                 185                 190

Glu Tyr Arg Cys Glu Ala Lys Asn Arg Leu Pro Asn Tyr Ala Thr Tyr
            195                 200                 205

Ser His Pro Val Thr Met Pro Ser Thr Gly Gly Asp Ser Cys Pro Phe
    210                 215                 220

Cys Leu Lys Leu Leu Leu Pro Gly Leu Leu Leu Leu Val Val Ile
225                 230                 235                 240

Ile Leu Ile Leu Ala Phe Trp Val Leu Pro Lys Tyr Lys Thr Arg Lys
                245                 250                 255

Ala Met Arg Asn Asn Val Pro Arg Asp Arg Gly Asp Thr Ala Met Glu
            260                 265                 270

Val Gly Ile Tyr Ala Asn Ile Leu Glu Lys Gln Ala Lys Glu Glu Ser
        275                 280                 285

Val Pro Glu Val Gly Ser Arg Pro Cys Val Ser Thr Ala Gln Asp Glu
290                 295                 300

Ala Lys His Ser Gln Glu Leu Gln Tyr Ala Thr Pro Val Phe Gln Glu
305                 310                 315                 320

Val Ala Pro Arg Glu Gln Glu Ala Cys Asp Ser Tyr Lys Ser Gly Tyr
                325                 330                 335

Val Tyr Ser Glu Leu Asn Phe
            340

<210> SEQ ID NO 2
<211> LENGTH: 248
<212> TYPE: PRT
<213> ORGANISM: Homo sapiens

<400> SEQUENCE: 2

Met Trp Ser His Leu Asn Arg Leu Leu Phe Trp Ser Ile Phe Ser Ser
1               5                   10                  15

Val Thr Cys Arg Lys Ala Val Leu Asp Cys Glu Ala Met Lys Thr Asn
            20                  25                  30

Glu Phe Pro Ser Pro Cys Leu Asp Ser Lys Thr Lys Val Val Met Lys
        35                  40                  45

Gly Gln Asn Val Ser Met Phe Cys Ser His Lys Asn Lys Ser Leu Gln
    50                  55                  60

Ile Thr Tyr Ser Leu Phe Arg Arg Lys Thr His Leu Gly Thr Gln Asp
65                  70                  75                  80

Gly Lys Gly Glu Pro Ala Ile Phe Asn Leu Ser Ile Thr Glu Ala His
                85                  90                  95

Glu Ser Gly Pro Tyr Lys Cys Lys Ala Gln Val Thr Ser Cys Ser Lys
            100                 105                 110
```

Tyr Ser Arg Asp Phe Ser Phe Thr Ile Val Gly Gly Asp Ser Cys Pro
            115                 120                 125

Phe Cys Leu Lys Leu Leu Pro Gly Leu Leu Leu Leu Val Val
        130                 135                 140

Ile Ile Leu Ile Leu Ala Phe Trp Val Leu Pro Lys Tyr Lys Thr Arg
145                 150                 155                 160

Lys Ala Met Arg Asn Asn Val Pro Arg Asp Arg Gly Asp Thr Ala Met
                165                 170                 175

Glu Val Gly Ile Tyr Ala Asn Ile Leu Glu Lys Gln Ala Lys Glu Glu
                180                 185                 190

Ser Val Pro Glu Val Gly Ser Arg Pro Cys Val Ser Thr Ala Gln Asp
                195                 200                 205

Glu Ala Lys His Ser Gln Glu Leu Gln Tyr Ala Thr Pro Val Phe Gln
                210                 215                 220

Glu Val Ala Pro Arg Glu Gln Glu Ala Cys Asp Ser Tyr Lys Ser Gly
225                 230                 235                 240

Tyr Val Tyr Ser Glu Leu Asn Phe
                245

<210> SEQ ID NO 3
<211> LENGTH: 253
<212> TYPE: PRT
<213> ORGANISM: Homo sapiens

<400> SEQUENCE: 3

Met Trp Ser His Leu Asn Arg Leu Leu Phe Trp Ser Ile Phe Ser Ser
1               5                   10                  15

Val Thr Cys Arg Lys Ala Val Leu Asp Cys Glu Ala Met Lys Thr Asn
                20                  25                  30

Asp Pro Val Thr Ser Pro Val Leu Asn Ile Met Val Ile Gln Thr Glu
                35                  40                  45

Thr Asp Arg His Ile Thr Leu His Cys Leu Ser Val Asn Gly Ser Leu
50                  55                  60

Pro Ile Asn Tyr Thr Phe Phe Glu Asn His Val Ala Ile Ser Pro Ala
65                  70                  75                  80

Ile Ser Lys Tyr Asp Arg Glu Pro Ala Glu Phe Asn Leu Thr Lys Lys
                85                  90                  95

Asn Pro Gly Glu Glu Glu Tyr Arg Cys Glu Ala Lys Asn Arg Leu
                100                 105                 110

Pro Asn Tyr Ala Thr Tyr Ser His Pro Val Thr Met Pro Ser Thr Gly
                115                 120                 125

Gly Asp Ser Cys Pro Phe Cys Leu Lys Leu Leu Pro Gly Leu Leu
                130                 135                 140

Leu Leu Leu Val Val Ile Ile Leu Ile Leu Ala Phe Trp Val Leu Pro
145                 150                 155                 160

Lys Tyr Lys Thr Arg Lys Ala Met Arg Asn Asn Val Pro Arg Asp Arg
                165                 170                 175

Gly Asp Thr Ala Met Glu Val Gly Ile Tyr Ala Asn Ile Leu Glu Lys
                180                 185                 190

Gln Ala Lys Glu Glu Ser Val Pro Glu Val Gly Ser Arg Pro Cys Val
                195                 200                 205

Ser Thr Ala Gln Asp Glu Ala Lys His Ser Gln Glu Leu Gln Tyr Ala
210                 215                 220

Thr Pro Val Phe Gln Glu Val Ala Pro Arg Glu Gln Glu Ala Cys Asp
225                 230                 235                 240

Ser Tyr Lys Ser Gly Tyr Val Tyr Ser Glu Leu Asn Phe
                245                 250

<210> SEQ ID NO 4
<211> LENGTH: 246
<212> TYPE: PRT
<213> ORGANISM: Mus musculus

<400> SEQUENCE: 4

Met Gly Asp Gly Asp Ser Pro Met Cys Leu Ser Ala Val Ser Phe Lys
1               5                   10                  15

Gly Ile Arg Cys Trp Leu Asp Lys Leu Leu Leu Trp Ala Leu Thr Ile
                20                  25                  30

Ser Ile Thr Leu Gln Asn Ala Ala Val Asp Cys Thr Arg Val Glu Asn
                35                  40                  45

Asn Glu Leu Pro Ser Pro Asn Leu Asn Ser Ser Met Asn Val Val Arg
            50                  55                  60

Met Gly Gln Asn Val Ser Leu Ser Cys Ser Thr Lys Asn Thr Ser Val
65                  70                  75                  80

Asp Ile Thr Tyr Ser Leu Phe Trp Gly Thr Lys Tyr Leu Glu Ser Lys
                85                  90                  95

Arg Arg Arg Gly Gly Ala Val Asp Phe His Leu Arg Ile Ser Asn Ala
                100                 105                 110

Asn Glu Ser Gly Pro Tyr Lys Cys Lys Val Asn Val Ser Asn Leu Met
            115                 120                 125

Lys Tyr Ser Gln Asp Phe Asn Phe Thr Met Ala Lys Asp Glu Ser Cys
130                 135                 140

Pro Ser Cys Arg Leu Ser Leu Leu Pro Gly Leu Leu Leu Gly Ile
145                 150                 155                 160

Leu Val Ile Val Leu Val Leu Ala Tyr Leu Ile His Leu Lys Tyr Lys
                165                 170                 175

Lys Gly Lys Lys Thr Gln Arg Glu Asp Gln Ser Lys Gly Ser Gly Asp
                180                 185                 190

Ala Pro Ala Gln Asp Glu Leu Tyr Val Asn Ala Cys Lys Thr Gln Thr
            195                 200                 205

Glu Gln Pro Gln Glu Ile His Tyr Ala Thr Pro Val Phe Lys Glu Met
210                 215                 220

Ala Pro Met Glu Glu Glu Gly Gly Thr Asp Gly Lys Ala Asp Tyr Ile
225                 230                 235                 240

Tyr Ser Glu Leu Thr His
                245

<210> SEQ ID NO 5
<211> LENGTH: 1448
<212> TYPE: DNA
<213> ORGANISM: Homo sapiens

<400> SEQUENCE: 5
accactgtgg ttctactatg ccttctgacc ccgtcttgga cttcaactgg gagaatgtgg      60
agccatttga acaggctcct cttctggagc atattttctt ctgtcacttg tagaaaagct     120
gtattggatt gtgaggcaat gaaaacaaat gaattccctt ctccatgttt ggactcaaag     180
actaaggtgg ttatgaaggg tcaaaatgta tctatgtttt gttcccataa gaacaaatca     240

```
ctgcagatca cctattcatt gtttcgacgt aagacacacc tgggaaccca ggatggaaaa    300
ggtgaacctg cgatttttaa cctaagcatc acagaagccc atgaatcagg ccctacaaa    360 tgcaaagccc aagttaccag ctgttcaaaa tacagtcgtg acttcagctt cacgattgtc    420
gacccggtga cttccccagt gctgaacatt atggtcattc aaacagaaac agaccgacat    480
ataacattac attgcctctc agtcaatggc tcgctgccca tcaattacac tttctttgaa    540
aaccatgttg ccatatcacc agctatttcc aagtatgaca gggagcctgc tgaatttaac    600
ttaaccaaga gaatcctggg agaagaggaa gagtataggt gtgaagctaa aaacagattg    660
cctaactatg caacatacag tcaccctgtc accatgccct caacaggcgg agacagctgt    720
cctttctgtc tgaagctact acttccaggg ttattactgt tgctggtggt gataatccta    780
attctggctt tttgggtact gcccaaatac aaaacaagaa aagctatgag aaataatgtg    840
cccagggacc gtggagacac agccatggaa gttggaatct atgcaaatat ccttgaaaaa    900
caagcaaagg aggaatctgt gccagaagtg ggatccaggc cgtgtgtttc cacagcccaa    960
gatgaggcca aacactccca ggagctacag tatgccaccc ccgtgttcca ggaggtggca   1020
ccaagagagc aagaagcctg tgattcttat aaatctggat atgtctattc tgaactcaac   1080
ttctgaaatt tacagaaaca aactacatct caggatggag tctcactctg ttgcccaggc   1140
tggagttcag tagcgcgatc ttggctcact tcaatctcca tcttcccagt tcaagcgatt   1200
ctcatgcctc gacctcccga gtagctggga ttacaggtgc ccgctaccac gcccagctaa   1260 ttttttgtatt tttagtagag atggggtttc actatggtgg ccaggctggt cttgaactcc   1320
tgacctcaga tgatctgcct gcctcggcct cccaaagtgc tggaactaca gcctgagcc   1380 accgtgcccg ccctgaatc gctttagtaa ataaagggtc tccaagaata aattcatccg   1440
aacatgca                                                           1448

<210> SEQ ID NO 6
<211> LENGTH: 747
<212> TYPE: DNA
<213> ORGANISM: Homo sapiens

<400> SEQUENCE: 6
atgtggagcc atttgaacag gctcctcttc tggagcatat tttcttctgt cacttgtaga     60
aaagctgtat ggattgtga ggcaatgaaa acaaatgaat tcccttctcc atgtttggac    120
tcaaagacta aggtggttat gaagggtcaa atgtatccta tgttttgttc ccataagaac    180
aaatcactgc agatcaccta ttcattgttt cgacgtaaga cacacctggg aacccaggat    240
ggaaaaggtg aacctgcgat ttttaaccta agcatcacag aagcccatga atcaggcccc    300
tacaaatgca agcccaagt taccagctgt tcaaaataca gtcgtgactt cagcttcacg    360
attgtcggcg gagacagctg tccttctgt ctgaagctac tacttccagg ttattactg    420 ttgctggtgg tgataatcct aattctggct ttttgggtac tgcccaaata caaaacaaga    480
aaagctatga gaataatgt gcccagggac cgtggagaca cagccatgga agttggaatc    540
tatgcaaata tccttgaaaa acaagcaaag gaggaatctg tgccagaagt gggatccagg    600
ccgtgtgttt ccacagccca agatgaggcc aaacactccc aggagctaca gtatgccacc    660
cccgtgttcc aggaggtggc accaagagag caagaagcct gtgattctta taaatctgga    720
tatgtctatt ctgaactcaa cttctga                                      747

<210> SEQ ID NO 7
<211> LENGTH: 762
```

```
<212> TYPE: DNA
<213> ORGANISM: Homo sapiens

<400> SEQUENCE: 7
atgtggagcc atttgaacag gctcctcttc tggagcatat tttcttctgt cacttgtaga      60
aaagctgtat tggattgtga ggcaatgaaa acaaatgacc cggtgacttc cccagtgctg     120
aacattatgg tcattcaaac agaaacagac cgacatataa cattacattg cctctcagtc     180
aatggctcgc tgcccatcaa ttacactttc tttgaaaacc atgttgccat atcaccagct     240
atttccaagt atgacaggga gcctgctgaa tttaacttaa ccaagaagaa tcctggagaa     300
gaggaagagt ataggtgtga agctaaaaac agattgccta actatgcaac atacagtcac     360
cctgtcacca tgccctcaac aggcggagac agctgtcctt tctgtctgaa gctactactt     420
ccagggttat tactgttgct ggtggtgata tcctaattc tggctttttg ggtactgccc      480
aaatacaaaa caagaaaagc tatgagaaat aatgtgccca gggaccgtgg agacacagcc     540
atggaagttg gaatctatgc aaatatcctt gaaaaacaag caaaggagga atctgtgcca     600
gaagtgggat ccaggccgtg tgtttccaca gcccaagatg aggccaaaca ctcccaggag     660
ctacagtatg ccacccccgt gttccaggag gtggcaccaa gagagcaaga agcctgtgat     720
tcttataaat ctggatatgt ctattctgaa ctcaacttct ga                         762

<210> SEQ ID NO 8
<211> LENGTH: 1320
<212> TYPE: DNA
<213> ORGANISM: Mus musculus

<400> SEQUENCE: 8
agtaactcaa ttaaccatgg gcgatggtga ctcgccaatg tgcctctctg ccgtttcatt      60
caagggaata agatgctggc tggacaaact gttactttgg gctcttacaa tttctatcac     120
acttcagaat gctgcagtgg attgtacgag ggtggaaaat aacgaattac cttctccaaa     180
tctgaactca agtatgaacg tggtcaggat gggccaaaat gtatctctgt cttgttccac     240
caagaacaca tcagtagaca tcacctattc gctcttctgg ggtacaaaat atctagaaag     300
caagagaaga cgagggggag ctgtggattt ccacctgagg atctccaatg ccaacgagtc     360
aggcccctac aaatgcaaag tcaatgtttc caacttgatg aaatacagtc aggatttcaa     420
cttcacaatg gccaaagatg agagctgccc ttcatgccgg ctgtcactgt tgctcccagg     480
gctgttactg gggatactgg taatagtcct agttctggct tatttgattc atctaaaata     540
caaaaaagga agaagactc agagagagga ccagtccaag ggttctggag atgcgcctgc      600
acaggacgag ctgtatgtca cgcctgcaa gactcagaca gagcaacccc aggagataca     660
ctatgccact ccagtcttca aggagatggc acccatggaa gaagaaggtg gtacggatgg     720
aaaagctgat tacatctact ctgaactcac ccactgaagt gtgaagaaac tgactgtatc     780
ccagtgtaaa gactttccag taagctgtgt atgagaaaat aggaaactca cctggcactt     840
aagagttcca ttctaggctg aggcaggagg atcctgagtt tgaggccagc tgggactaca     900
tagcaaggcc ttgtcttaaa acacaaaatc aaaaaaagat ttaacctggt cacctatagt     960
gagtgtatt tacacatctg acactatttt ctttggctaa tttgggcact aatcttgtta    1020
tccaagtagc caggcttgat aagagttaaa acatacttag gttttgtggc cttccacctt    1080
ctcccttccc aacacaatta tcttgggacc gaggaggtgg ttcagcagtt aagagcagac    1140
actagggctg gtgagatggc tctgtgggta agagcacgga ctgttcttcc atcaaggtcc    1200
```

```
tgagttcaaa tcccagcaac cacatggtgg ctcacaacca accataataa gatctgatgc    1260
cctcttctgg cgcatctgaa gacagctaca gtgtatttat gtataataat aaataaatct    1320
```

IMMUNITY ENHANCING AGENT FOR CANCER BY ALLERGIN-1 ANTAGONIST

TECHNICAL FIELD

The present invention relates to an immunity enhancing agent for cancer, containing an Allergin-1 antagonist as an active ingredient. More specifically, the present invention relates to an agent for suppression of progress of, suppression of recurrence of and/or treatment of cancer, characterized by administration of an Allergin-1 antagonist alone or a combination thereof with an anti-cancer agent.

BACKGROUND ART

Different from conventional therapies by surgery, radiotherapy or drug therapy by anti-cancer agents or molecular targeting agents, cancer immunotherapy is to suppress progress of cancer or treat cancer by acting on the immune surveillance intrinsic to cancer patients, thereby enhancing the immunity against cancer. As a result of recent researches on cancer immunity, it has been elucidated that the immunosuppressive environment surrounding a cancer site is involved in progress of cancer and cancer per se utilizes the system for avoiding the immune surveillance. As the molecules utilized for the avoidance system, so-called immune checkpoint molecules such as CTLA-4 and PD-1 or PD-L1, which is a ligand thereof, are known (PTL 1 and 2), and the inhibitors have already exhibited significant clinical results.

However, it is also true that there are still cancer patients for whom sufficient therapeutic effects are not observed even with the immune checkpoint inhibitors. Thus, there is an urgent need for novel therapies for the cancer patients and functional understanding of target molecules crucial for establishment of the therapies.

Meanwhile, Allergin-1 involved in the present invention is a membrane-associated receptor having an ITIM domain in the intracellular region and an extracellular immunoglobulin-like structure and is strongly expressed on mast cells. It is known from analyses of the molecule using knockout mice that the molecule suppresses allergic reactions such as suppressing degranulation via IgE receptor signalling, thereby suppressing anaphylaxis, or suppressing asthma reaction induced by mite allergens (NPL 1, 2 and 3).

However, it is not sufficiently known that the molecule suppresses cancer immunity.

CITATION LIST

Patent Literatures

[PTL 1] WO 2006/121168
[PTL 2] Japanese Patent Application Publication No. 2006-340714

Non Patent Literature

[NPL 1] Nature Immunology, 2010, Vol. 11, No. 7, p. 601-608
[NPL 2] PLOS ONE, 2013, Vol. 8, No. 10, e76160
[NPL 3] Allergology & Immunology, 2011, Vol. 18, No. 4, p. 506-514

SUMMARY OF INVENTION

Technical Problem

An object of the present invention is to provide an agent for suppression of progress of, suppression of recurrence of and/or treatment of cancer, containing a novel active ingredient capable of enhancing the immunity against cancer.

Solution to Problem

The inventors of the present invention carried out extensive studies and as a result, found out that an antagonist to Allergin-1 can solve the above problem, thereby completing the present invention.

Thus, the present invention is as follows:

[1] An immunity enhancing agent for cancer, containing an Allergin-1 antagonist as an active ingredient.
[2] The agent according to the preceding item [1], for use in suppression of progress of, suppression of recurrence of and/or treatment of cancer.
[3] An agent for suppression of progress of, suppression of recurrence of and/or treatment of cancer, containing an Allergin-1 antagonist as an active ingredient.
[4] The agent according to any one of the preceding items [1] to [3], wherein the Allergin-1 antagonist suppresses immunosuppressive intracellular signalling of Allergin-1.
[5] The agent according to any one of the preceding items [1] to [4], wherein the Allergin-1 antagonist is an anti-Allergin-1 antibody, an Allergin-1 binding protein or an Allergin-1-fusion protein.
[6] The agent according to the preceding item [5], wherein the anti-Allergin-1 antibody is an anti-human Allergin-1 antibody.
[7] The agent according to the preceding item [5] or [6], wherein the anti-Allergin-1 antibody is a monoclonal antibody.
[8] The agent according to the preceding item [7], wherein the anti-Allergin-1 monoclonal antibody is of $IgG_1$ or $IgG_4$ isotype.
[9] The agent according to the preceding item [7] or [8], wherein the anti-Allergin-1 monoclonal antibody is an antibody fragment selected from the group consisting of Fab, Fab', Fv, scFv and $(Fab')_2$ fragments.
[10] The agent according to any one of the preceding items [7] to [9], wherein the anti-Allergin-1 monoclonal antibody is a humanized or human antibody.
[11] The agent according to the preceding item [7], wherein the anti-Allergin-1 monoclonal antibody is a humanized or human anti-human Allergin-1 monoclonal $IgG_1$ or $IgG_4$ antibody.
[12] The agent according to any one of the preceding items [7] to [11], wherein the anti-Allergin-1 monoclonal antibody binds to human Allergin-1 with Kd value of $5\times10^{-8}$ M or less.
[13] The agent according to any one of the preceding items [7] to [11], wherein the anti-Allergin-1 monoclonal antibody binds to human Allergin-1 with Kd value of $1\times10^{-8}$ M or less.
[14] The agent according to any one of the preceding items [7] to [11], wherein the anti-Allergin-1 monoclonal antibody binds to human Allergin-1 with Kd value of $5\times10^{-9}$ M or less.
[15] The agent according to any one of the preceding items [7] to [11], wherein the anti-Allergin-1 monoclonal antibody binds to human Allergin-1 with Kd value of $1\times10^{-9}$ M or less.
[16] The agent according to the preceding item [5] or [6], wherein the anti-Allergin-1 antibody is an Allergin-1 multispecific antibody recognizing two or more different epitopes present on one Allergin-1 molecule.

[17] The agent according to any one of the preceding items [2] to [16], wherein the cancer is solid cancer or hematologic cancer.

[18] The agent according to the preceding item [17], wherein the solid cancer is one or more cancers selected from malignant melanoma, non-small cell lung cancer, small cell lung cancer, head and neck cancer, renal cell cancer, clear cell renal cell cancer, breast cancer, ovarian cancer, ovarian clear cell adenocarcinoma, bone and soft tissue sarcoma, glioblastoma, gliosarcoma, nasopharyngeal cancer, uterine cancer, anal cancer, colorectal cancer, hepatocellular cancer, esophageal cancer, pancreatic cancer, stomach cancer, urothelial cancer, prostate cancer, fallopian tube cancer, primary peritoneal cancer, pleural mesothelioma and myeloproliferative syndrome.

[19] The agent according to the preceding item [17], wherein the hematologic cancer is one or more cancers selected from multiple myeloma, non-Hodgkin lymphoma, Hodgkin lymphoma, acute myeloid leukaemia and chronic myeloid leukaemia.

[20] The agent according to any one of the preceding items [2] to [19], which is administered to a cancer patient with insufficient therapeutic efficacy by an anti-cancer drug.

[21] The agent according to the preceding item [20], wherein the anti-cancer drug is a tumor immunotherapeutic agent.

[22] The agent according to the preceding item [21], wherein the tumor immunotherapeutic agent is one or more drugs selected from an anti-PD-1 antibody, an anti-PD-L1 antibody, an anti-PD-L2 antibody, a PD-L1 fusion protein, a PD-L2 fusion protein, an anti-CTLA-4 antibody, an anti-LAG-3 antibody, an anti-Tim3 antibody, an anti-KIR antibody, an anti-BTLA antibody, an anti-TIGIT antibody, an anti-VISTA antibody, an anti-CD137 antibody, an anti-OX40 antibody, an anti-HVEM antibody, an anti-CD27 antibody, an anti-GITR antibody, an anti-CD28 antibody, an anti-CCR4 antibody and an anti-CD4 antibody.

[23] The agent according to the preceding item [22], wherein the anti-PD-1 antibody is Nivolumab, REGN-2810, Pembrolizumab, PDR-001, BGB-A317, STI-A1110 or AMP-514.

[24] The agent according to the preceding item [22], wherein the anti-PD-L1 antibody is Atezolizumab, Avelumab, Durvalumab or BMS-936559.

[25] The agent according to the preceding item [22], wherein the anti-CTLA-4 antibody is Ipilimumab or Tremelimumab.

[26] The agent according to the preceding item [22], wherein the PD-L2 fusion protein is AMP-224.

[27] The agent according to any one of the preceding items [1] to [26], wherein one or more anti-cancer drugs are further administered.

[28] The agent according to the preceding item [27], wherein the Allergin-1 antagonist and the anti-cancer drug in different preparations are administered.

[29] The agent according to the preceding item [28], wherein the anti-cancer drug is administered prior to administration of the Allergin-1 antagonist.

[30] The agent according to the preceding item [28], wherein the Allergin-1 antagonist is administered prior to administration of the anti-cancer drug.

[31] The agent according to any one of the preceding items [27] to [30], wherein there is a period when the Allergin-1 antagonist and the anti-cancer drug are administered simultaneously.

[32] The agent according to the preceding item [27] or [28], wherein the Allergin-1 antagonist and the anti-cancer drug are administered simultaneously.

[33] The agent according to the preceding items [27] or [32], wherein the Allergin-1 antagonist and the anti-cancer drug in one preparation is administered.

[34] The agent according to any one of the preceding items [27] to [33], wherein the anti-cancer drug is a tumor immunotherapeutic agent.

[35] The agent according to the preceding item [34], wherein the tumor immunotherapeutic agent is one or more selected from an anti-PD-1 antibody, an anti-PD-L1 antibody, an anti-PD-L2 antibody, a PD-L1 fusion protein, a PD-L2 fusion protein, an anti-CTLA-4 antibody, an anti-LAG-3 antibody, an anti-Tim3 antibody, an anti-KIR antibody, an anti-BTLA antibody, an anti-TIGIT antibody, an anti-VISTA antibody, an anti-CD137 antibody, an anti-OX40 antibody, an anti-HVEM antibody, an anti-CD27 antibody, an anti-GITR antibody, an anti-CD28 antibody, an anti-CCR4 antibody and an anti-CD4 antibody.

[36] The agent according to the preceding item [35], wherein the anti-PD-1 antibody is Nivolumab, REGN-2810, Pembrolizumab, PDR-001, BGB-A317, STI-A1110 or AMP-514.

[37] The agent according to the preceding item [35], wherein the anti-PD-L1 antibody is Atezolizumab, Avelumab, Durvalumab or BMS-936559.

[38] The agent according to the preceding item [35], wherein the anti-CTLA-4 antibody is Ipilimumab or Tremelimumab.

[39] The agent according to the preceding item [35], wherein the PD-L2 fusion protein is AMP-224.

[40] The agent according to the preceding item [35], wherein the anti-CD4 antibody is. IT1208.

[41] The agent according to any one of the preceding items [1] to [40], wherein the Allergin-1 antagonist enhances production of type I interferon (such as interferon-α and/or interferon-β).

[42] The agent according to any one of the preceding item [1] to [41], wherein the Allergin-1 antagonist stimulates proliferation of CD8 positive T cells.

[43] The agent according to any one of the preceding items [1] to [42], wherein the Allergin-1 antagonist activates CD8 positive T cells.

[44] An immunity enhancing agent for cancer, containing a human or humanized anti-human Allergin-1 monoclonal IgG$_1$ or IgG$_4$ antibody as an active ingredient, wherein the cancer is/are one or more selected from malignant melanoma, non-small cell lung cancer, small cell lung cancer, head and neck cancer, renal cell cancer, clear cell renal cell cancer, breast cancer, ovarian cancer, ovarian clear cell adenocarcinoma, bone and soft tissue sarcoma, glioblastoma, gliosarcoma, nasopharyngeal cancer, uterine cancer, anal cancer, colorectal cancer, hepatocellular cancer, esophageal cancer, pancreatic cancer, stomach cancer, urothelial cancer, prostate cancer, fallopian tube cancer, primary peritoneal cancer, pleural mesothelioma and myeloproliferative syndrome.

[45] An immunity enhancing agent for cancer, containing a human or humanized anti-human Allergin-1 monoclonal IgG$_1$ or IgG$_4$ antibody as an active ingredient, wherein the cancer is/are one or more selected from multiple myeloma, malignant lymphoma (such as non-Hodgkin lymphoma (such as follicular lymphoma and diffuse large B-cell lymphoma) and Hodgkin lymphoma) and leukaemia (such as acute myeloid leukaemia and chronic myeloid leukaemia).

[46] An agent for suppression of progress of, suppression of recurrence of and/or treatment of cancer, containing a human or humanized anti-human Allergin-1 monoclonal IgG$_1$ or IgG$_4$ antibody as an active ingredient, wherein the cancer is/are one or more selected from malignant melanoma, non-small cell lung cancer, small cell lung cancer, head and neck cancer, renal cell cancer, clear cell renal cell cancer, breast cancer, ovarian cancer, ovarian clear cell adenocarcinoma, bone and soft tissue sarcoma, glioblastoma, gliosarcoma, nasopharyngeal cancer, uterine cancer, anal cancer, colorectal cancer, hepatocellular cancer, esophageal cancer, pancreatic cancer, stomach cancer, urothelial cancer, prostate cancer, fallopian tube cancer, primary peritoneal cancer, pleural mesothelioma and myeloproliferative syndrome.

[47] An agent for suppression of progress of, suppression of recurrence of and/or treatment of cancer, containing a human or humanized anti-human Allergin-1 monoclonal IgG$_1$ or IgG$_4$ antibody as an active ingredient, wherein the cancer is/are one or more selected from multiple myeloma, malignant lymphoma (such as non-Hodgkin lymphoma (such as follicular lymphoma and diffuse large B-cell lymphoma) and Hodgkin lymphoma) and leukaemia (such as acute myeloid leukaemia and chronic myeloid leukaemia).

[48] An agent for suppression of progress of, suppression of recurrence of and/or treatment of cancer, containing a human or humanized anti-human Allergin-1 monoclonal IgG$_1$ or IgG$_4$ antibody as an active ingredient, wherein the agent is administered to a cancer patient with insufficient therapeutic efficacy by a tumor immunotherapeutic agent, and wherein the cancer is/are one or more selected from malignant melanoma, non-small cell lung cancer, small cell lung cancer, head and neck cancer, renal cell cancer, clear cell renal cell cancer, breast cancer, ovarian cancer, ovarian clear cell adenocarcinoma, bone and soft tissue sarcoma, glioblastoma, gliosarcoma, nasopharyngeal cancer, uterine cancer, anal cancer, colorectal cancer, hepatocellular cancer, esophageal cancer, pancreatic cancer, stomach cancer, urothelial cancer, prostate cancer, fallopian tube cancer, primary peritoneal cancer, pleural mesothelioma and myeloproliferative syndrome.

[49] An agent for suppression of progress of, suppression of recurrence of and/or treatment of cancer, containing a human or humanized anti-human Allergin-1 monoclonal IgG$_1$ or IgG$_4$ antibody as an active ingredient, wherein the agent is administered to a cancer patient with insufficient therapeutic efficacy by a tumor immunotherapeutic agent, and wherein the cancer is/are one or more selected from multiple myeloma, malignant lymphoma (such as non-Hodgkin lymphoma (such as follicular lymphoma and diffuse large B-cell lymphoma) and Hodgkin lymphoma) and leukaemia (such as acute myeloid leukaemia and chronic myeloid leukaemia).

[50] An agent for suppression of progress of, suppression of recurrence of and/or treatment of one or more cancers selected from malignant melanoma, non-small cell lung cancer, small cell lung cancer, head and neck cancer, renal cell cancer, clear cell renal cell cancer, breast cancer, ovarian cancer, ovarian clear cell adenocarcinoma, bone and soft tissue sarcoma, glioblastoma, gliosarcoma, nasopharyngeal cancer, uterine cancer, anal cancer, colorectal cancer, hepatocellular cancer, esophageal cancer, pancreatic cancer, stomach cancer, urothelial cancer, prostate cancer, fallopian tube cancer, primary peritoneal cancer, pleural mesothelioma and myeloproliferative syndrome, containing a human or humanized anti-human Allergin-1 monoclonal IgG$_1$ or IgG$_4$ antibody as an active ingredient, wherein the agent is administered with one or more tumor immunotherapeutic agents selected from an anti-PD-1 antibody, an anti-PD-L1 antibody, an anti-PD-L2 antibody, a PD-L1 fusion protein, a PD-L2 fusion protein, an anti-CTLA-4 antibody, an anti-LAG-3 antibody, an anti-Tim3 antibody, an anti-KIR antibody, an anti-BTLA antibody, an anti-TIGIT antibody, an anti-VISTA antibody, an anti-CD137 antibody, an anti-OX40 antibody, an anti-HVEM antibody, an anti-CD27 antibody, an anti-GITR antibody, an anti-CD28 antibody, an anti-CCR4 antibody and an anti-CD4 antibody.

[51] An agent for suppression of progress of, suppression of recurrence of and/or treatment of one or more cancers selected from multiple myeloma, malignant lymphoma (such as non-Hodgkin lymphoma (such as follicular lymphoma and diffuse large B-cell lymphoma) and Hodgkin lymphoma) and leukaemia (such as acute myeloid leukaemia and chronic myeloid leukaemia), containing a human or humanized anti-human Allergin-1 monoclonal IgG$_1$ or IgG$_4$ antibody as an active ingredient, wherein the agent is administered with one or more tumor immunotherapeutic agents selected from an anti-PD-1 antibody, an anti-PD-L1 antibody, an anti-PD-L2 antibody, a PD-L1 fusion protein, a PD-L2 fusion protein, an anti-CTLA-4 antibody, an anti-LAG-3 antibody, an anti-Tim3 antibody, an anti-KIR antibody, an anti-BTLA antibody, an anti-TIGIT antibody, an anti-VISTA antibody, an anti-CD137 antibody, an anti-OX40 antibody, an anti-HVEM antibody, an anti-CD27 antibody, an anti-GITR antibody, an anti-CD28 antibody, an anti-CCR4 antibody and an anti-CD4 antibody.

[52] An agent for suppression of progress of, suppression of recurrence of and/or treatment of one or more cancers selected from malignant melanoma, non-small cell lung cancer, small cell lung cancer, head and neck cancer, renal cell cancer, clear cell renal cell cancer, breast cancer, ovarian cancer, ovarian clear cell adenocarcinoma, bone and soft tissue sarcoma, glioblastoma, gliosarcoma, nasopharyngeal cancer, uterine cancer, anal cancer, colorectal cancer, hepatocellular cancer, esophageal cancer, pancreatic cancer, stomach cancer, urothelial cancer, prostate cancer, fallopian tube cancer, primary peritoneal cancer, pleural mesothelioma and myeloproliferative syndrome, containing a human or humanized anti-human Allergin-1 monoclonal IgG$_1$ or IgG$_4$ antibody as an active ingredient, wherein the agent is administered with one or more anti-PD-1 antibodies selected from Nivolumab, REGN-2810, Pembrolizumab, PDR-001, BGB-A317, AMP-514, ANB011 and STI-A1110.

[53] An agent for suppression of progress of, suppression of recurrence of and/or treatment of one or more cancers selected from multiple myeloma, malignant lymphoma (such as non-Hodgkin lymphoma (such as follicular lymphoma and diffuse large B-cell lymphoma) and Hodgkin lymphoma) and leukaemia (such as acute myeloid leukaemia and chronic myeloid leukaemia), containing a human or humanized anti-human Allergin-1 monoclonal IgG$_1$ or IgG$_4$ antibody as an active ingredient, wherein the agent is administered with one or more anti-PD-1 antibodies selected from Nivolumab, REGN-2810, Pembrolizumab, PDR-001, BGB-A317, AMP-514, ANB011 and STI-A1110.

[54] An agent for suppression of progress of, suppression of recurrence of and/or treatment of one or more cancers selected from malignant melanoma, non-small cell lung cancer, small cell lung cancer, head and neck cancer, renal cell cancer, clear cell renal cell cancer, breast cancer, ovarian cancer, ovarian clear cell adenocarcinoma, bone and soft tissue sarcoma, glioblastoma, gliosarcoma, nasopharyngeal cancer, uterine cancer, anal cancer, colorectal cancer, hepatocellular cancer, esophageal cancer, pancreatic cancer, stomach cancer, urothelial cancer, prostate cancer, fallopian tube cancer, primary peritoneal cancer, pleural mesothelioma and myeloproliferative syndrome, containing a human or humanized anti-human Allergin-1 monoclonal IgG$_1$ or IgG$_4$ antibody as an active ingredient, wherein the agent is administered with one or more anti-PD-L1 antibodies selected from Atezolizumab, Avelumab, Durvalumab and BMS-936559.

[55] An agent for suppression of progress of, suppression of recurrence of and/or treatment of one or more cancers selected from multiple myeloma, malignant lymphoma (such as non-Hodgkin lymphoma (such as follicular lymphoma and diffuse large B-cell lymphoma) and Hodgkin lymphoma) and leukaemia (such as acute myeloid leukaemia and chronic myeloid leukaemia), containing a human or humanized anti-human Allergin-1 monoclonal $IgG_1$ or $IgG_4$ antibody as an active ingredient, wherein the agent is administered with one or more anti-PD-L1 antibodies selected from Atezolizumab, Avelumab, Durvalumab and BMS-936559.

[56] An Allergin-1 antagonist for enhancing the immunity against cancer.

[57] Use of an Allergin-1 antagonist in production of an immunity enhancing agent for cancer.

[58] A method for enhancing the immunity against cancer, comprising administering an effective dosage of an Allergin-1 antagonist to a patient in need of cancer therapy.

[59] An Allergin-1 antagonist for suppression of progress of, suppression of recurrence of and/or treatment of cancer.

[60] Use of an Allergin-1 antagonist in production of an agent for suppression of progress of, suppression of recurrence of and/or treatment of cancer.

[61] A method for suppressing progress of, suppressing recurrence of and/or treating cancer, comprising administering an effective dosage of an Allergin-1 antagonist to a patient in need of cancer therapy.

Advantageous Effects of Invention

The Allergin-1 antagonist according to the present invention is capable of enhancing the immunity against cancer and may be used for suppression of progress of, suppression of recurrence of and/or treatment of cancer.

DESCRIPTION OF EMBODIMENTS

Figure 1:
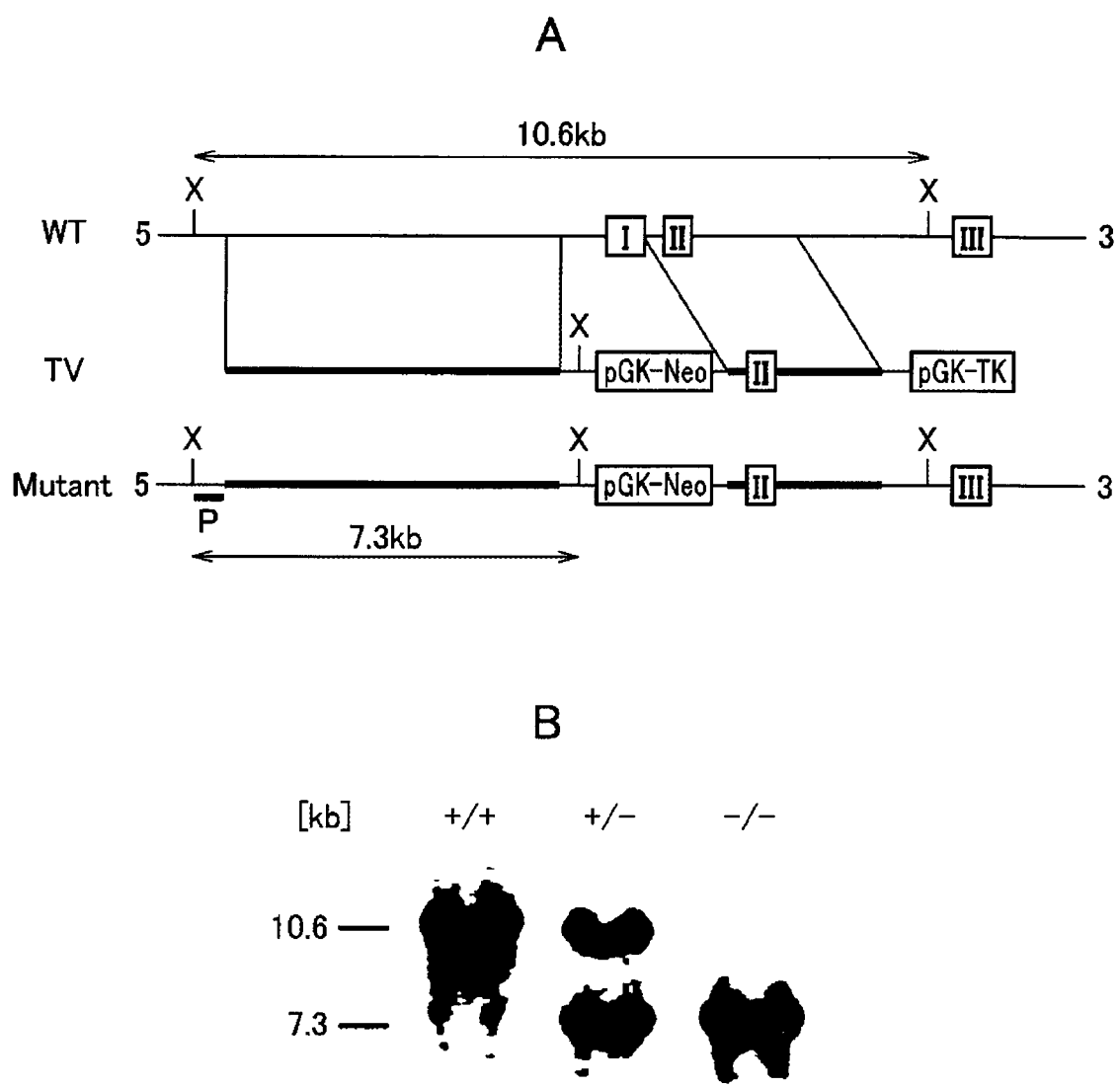
FIG. 1 shows the structure of an Allergin-1 targeting vector and the results of Southern blotting of generated Allergin-1 knockout (hereinafter also referred to as Allergin-1KO or Alg1-KO) heterozygous and homozygous mice.

Allergin-1 is also denoted as MILR1 and includes three splicing variants in humans which are "Allergin-1L", "Allergin-1S1" and "Allergin-1S2" which are membrane-associated proteins having amino acid sequences of SEQ ID NO: 1 (GenBank accession No. NP 001078892.11 SEQ ID NO: 2 (GenBank accession No. BAJ08252.1), and SEQ ID NO: 3 (GenBank accession No. BAJ08253.1), respectively. The mouse homologue thereof is denoted as MCA32 having an amino acid sequence of SEQ ID NO: 4 (GenBank accession No. BAJ08254.1). Genes encoding the above proteins have the sequences of GenBank accession nos. NM 001085423.2 (SEQ ID NO: 5), AB542951.1 (SEQ ID NO: 6), AB542952.1 (SEQ ID NO: 7), and AB542953.1 (SEQ ID NO: 8), respectively.

In the present specification, the term "Allergin-1" is used to include, unless otherwise stated, human Allergin-1 and splicing variants thereof as well as mammalian homologues identified by now.

As used herein, the term "Allergin-1 antagonist" means a substance which suppresses, decreases or completely inhibits intrinsic physiological functions of Allergin-1. Examples of the "Allergin-1 antagonist" include a substance which suppresses, decreases or completely inhibits immunosuppressive intracellular signalling of Allergin-1 by antagonizing a natural ligand of Allergin-1. Specifically, examples thereof include an anti-Allergin-1 antibody, an Allergin-1 fusion protein, an Allergin-1 binding protein, a peptide, a low molecular compound and the like. The Allergin-1 fusion protein means a protein molecule containing a whole or partial extracellular domain of Allergin-1, which suppresses, decreases or completely inhibits immunosuppressive intracellular signalling of Allergin-1 by antagonizing binding of, for example, a natural ligand of Allergin-1 to Allergin-1, and examples thereof include a whole or partial extracellular domain of Allergin-1 bound to an Fc region of an antibody. The Allergin-1 binding protein means a protein which binds to Allergin-1, antagonizes binding of, for example, a natural ligand of Allergin-1 to Allergin-1 and thus suppresses, decreases or completely inhibits immunosuppressive intracellular signalling of Allergin-1. Examples thereof include a natural ligand of Allergin-1, a whole or partial extracellular domain thereof, a fusion protein based on the foregoing, a scaffold protein and the like. Examples of the scaffold protein to Allergin-1 include Adnectin (WO 2001/64942), Affibody® (WO 95/19374, WO 2000/63243), Anticalin® (WO 99/16873), Avimer (Nature Biotechnology (2005), Vol. 23, pp. 1556-1561), DARPin (Nature Biotechnology (2004), Vol. 22, pp. 575-582), LRRP (Nature (2004), Vol. 430, No. 6996, pp. 174-180), Affilin® (WO 2001/04144 and WO 2004/106368), Affitin (Journal of molecular biology (2008), Vol. 383, No. 5, pp. 1058-1068), Fynomer (WO 2011/023685) and the like without limitation. Similarly to the Allergin-1 antagonist, an antisense RNA or siRNA (small interfering RNA) of Allergin-1, which inhibits gene expression or protein synthesis of Allergin-1, is also useful for suppressing, decreasing or completely inhibiting intrinsic physiological functions of Allergin-1.

Whether the anti-Allergin-1 antibody or Allergin-1 binding protein among the Allergin-1 antagonist according to the present invention antagonizes a natural ligand of Allergin-1 may be examined, for example, by the following method.

An Allergin-1 fusion protein is first prepared and a cell line which binds to the fusion protein is sought. With the cell line for which specific binding to the Allergin-1 fusion protein is confirmed, whether or not a substance is the Allergin-1 antagonist can be found by using, as an index, the presence or absence of antagonism of the Allergin-1 antagonist against binding of the Allergin-1 fusion protein to the cells. For example, an Allergin-1 fusion protein binds to a cell line THP-1 derived from human acute monocytic leukaemia, and an Allergin-1 antagonist may be obtained by monitoring an inhibitory activity on binding of the Allergin-1 fusion protein to THP-1.

As used herein, the term “antibody” includes a full-length antibody, namely a full-length antibody consisting of two heavy chains and two light chains linked via disulphide bonds, as well as an antibody fragment thereof (such as a single-stranded antibody (such as Fab, Fab', Fv and scFv) and $(Fab')_2$) and a multispecific antibody (such as a bispecific antibody and diabody).

As used herein, the term “monoclonal antibody” means an antibody consisting of a substantially uniform population having a single binding specificity toward a certain antigen. The monoclonal antibody used for the present invention may be prepared by the hybridoma method (for example, see Kohler and Milstein et al., Nature (1975), 256:495-97, Hongo et al., Hybridoma (1995), 14(3):253-260, Harlow et al., Antibodies: A Laboratory Manual, (Cold Spring Harbor Laboratory Press, second edition; 1988) and Hammerling et al., Monoclonal Antibodies and T-Cell Hybridomas, 563-681 (Elsevier, N.Y., 1981)), the recombinant DNA method (for example, see U.S. Pat. No. 4,816,567), the phage display method (for example, see U.S. Pat. Nos. 5,223,409, 5,403,484 and 5,571,698 by Ladner et al., U.S. Pat. Nos. 5,427,908 and 5,580,717 by Dower et al., U.S. Pat. Nos. 5,969,108 and 6,172,197 by McCafferty et al., and U.S. Pat. Nos. 5,885,793, 6,521,404, 6,544,731, 6,555,313, 6,582,915 and 6,593,081 by Griffiths et al.).

As used herein, the term “multispecific antibody” means an antibody molecule having binding specificity toward two or more different antigen molecules or epitopes and typically includes a bispecific antibody. The epitopes in this context may be epitopes on two or more different antigen molecules or two or more different epitopes present on one antigen molecule. Examples of embodiments of the bispecific antibody include a diabody, bispecific $sc(Fv)_2$, a bispecific minibody, bispecific F(ab')2, a bispecific hybrid antibody, a covalent diabody (bispecific DART) (WO 2006/113665 or WO 2008/157379), bispecific $(FvCys)_2$ (J. Immunol., 1992, Vol. 149, No. 1, p.120-126), a bispecific $F(ab'\text{-zipper})_2$ (J. Immunol., 1992, Vol. 148, No. 5, p.1547-1553), a bispecific $(Fv\text{-zipper})_2$ (Biochemistry, 1992, Vol. 31, No. 6, p.1579-1584), a bispecific three-chain antibody (Proc. Natl. Acad. Sci. USA, 1993, Vol. 90, No. 14, p.6444-6448) and a bispecific $mAb^2$ (f-star.com/technology_mab) and the like.

As used herein, the term “antibody fragment” means a part of a full-length antibody containing at least an antigen binding portion and examples thereof include Fab, Fab', Fv, scFv, F(ab')2 and the like. The antigen binding portion means a smallest unit of an antibody that can bind to an antigen and contains three complementarity-determining regions (CDRs) respectively in a heavy chain variable region and a light chain variable region and framework regions which arrange CDRs so that the combination of the CDRs can recognize a desired antigen.

As used herein, the term “chimeric antibody” means an antibody containing a variable region sequence and a constant region sequence respectively derived from different mammals. An example is one containing a variable region sequence derived from a mouse antibody and a constant region sequence derived from a human antibody. The chimeric antibody may be prepared by linking a gene encoding an antibody variable region isolated according to a well-known method from an antibody-producing hybridoma isolated according to the hybridoma method, recombinant DNA method or the phage display method described above to a gene encoding an antibody constant region gene derived from humans by a well-known method (for example, see U.S. Pat. No. 4,816,567 by Cabilly et al.).

As used herein, the term “humanized antibody” means an antibody containing CDR sequences derived from a germline of a mammal other than humans such as mice, grafted on human framework sequences. The humanized antibody may also be prepared by linking genes encoding antibody CDR regions isolated according to a well-known method from an antibody-producing hybridoma according to the above method to genes encoding antibody framework regions derived from humans by a well-known method (for example, see U.S. Pat. Nos. 5,225,539 and 5,530,101 by Winter and U.S. Pat. Nos. 5,585,089 and 6,180,370 by Queen).

As used herein, the term “human antibody” means an antibody containing a variable region formed with framework regions, CDR regions and a constant region, both of which are derived from a human germline immunoglobulin sequence. The human antibody used in the present invention may be prepared by a method in which mice transformed to produce a human antibody is used, such as Humab mice (for example, see U.S. Pat. Nos. 5,545,806, 5,569,825, 5,625,126, 5,633,425, 5,789,650, 5,877,397, 5,661,016, 5,814,318, 5,874,299 and 5,770,429 by Lonberg and Kay et al.), KM mice (for example, see WO 2002/43478 by Ishida et al.), XENOMOUSE® (for example, see U.S. Pat. Nos. 5,939,598, 6,075,181, 6,114,598, 6,150,584 and 6,162,963) and Tc mice (for example, see Tomizuka et al., Proc. Natl. Acad.

Sci. USA (2000):722-727). The human antibody may also be prepared by using SCID mice (for example, see U.S. Pat. Nos. 5,476,996 and 5,698,767 by Wilson et al.) in which human immune cells were reconstructed so as to trigger human antibody reaction by immunisation. The human antibody used in the present invention may also be prepared by the phage display method described above.

As used herein, the term "isotype" is used to denote an antibody class (such as IgM or IgG) encoded by a heavy chain constant region gene. The anti-Allergin-1 antibody according to the present invention is preferably $IgG_1$ or $IgG_4$. $IgG_1$ is preferably modified such that an arbitrary amino acid in the heavy chain constant region is substituted, deleted or inserted so that the antibody has eliminated or reduced binding to the Fc receptor. $IgG_4$ is preferably modified such that an arbitrary amino acid in the heavy chain constant region is substituted, deleted or inserted so that swapping is suppressed.

As used herein, the term "fusion protein" means a polypeptide having two protein moieties having different properties which are covalently linked. For example, when a membrane-associated protein is used for a fusion protein, a portion mainly containing an extracellular part of the membrane-associated protein may be bound to the Fc region of an antibody to obtain the fusion protein in order to promote solubilisation of the protein.

The anti-Allergin-1 antibody which may be selected as the Allergin-1 antagonist of the present invention is an antibody which binds to human Allergin-1 with a dissociation constant (Kd value) of $5 \times 10^{-8}$ M or less, more preferably binds to human Allergin-1 with Kd value of $1 \times 10^{-8}$ M or less, still more preferably binds to human Allergin-1 with Kd value of $5 \times 10^{-9}$ M or less and particularly preferably binds to human Allergin-1 with Kd value of $1 \times 10^{-9}$ M or less.

In another embodiment, the anti-Allergin-1 antibody is preferably an anti-human Allergin-1 multispecific antibody which recognizes two or more different epitopes present on one antigen molecule.

In still another embodiment, the anti-Allergin-1 antibody is preferably an anti-human Allergin-1 monoclonal antibody and still more preferably an anti-human Allergin-1 monoclonal $IgG_1$ or $IgG_4$ antibody.

As used herein, the term "cancer therapy" or the like encompasses, for example, a therapy which (i) reduces proliferation of cancer cells, (ii) attenuates a symptom resulting from cancer, (iii) improves the quality of life of a cancer patient, (iv) reduces the dose of another anti-cancer drug or cancer therapy adjuvant which has already been administered and/or (v) is to extend the survival of a cancer patient. The term "suppression of progress of cancer" means to delay the progress of cancer, stabilise a symptom associated with cancer and reverses the progress of a symptom. The term "suppression of recurrence" means to prophylactically prevent recurrence of cancer in a patient whose cancer lesion has been completely or substantially eliminated or removed by cancer therapy or cancer excision.

The cancer which may be subjected to suppression of progress, suppression of recurrence and/or treatment with the Allergin-1 antagonist includes any solid cancer and hematologic cancer. Examples of the solid cancer for which the Allergin-1 antagonist may be particularly effective include malignant melanoma (such as malignant melanoma in the skin, oral mucosa epithelial and intraorbital), non-small cell lung cancer (such as squamous non-small cell lung cancer and non-squamous non-small cell lung cancer), small cell lung cancer, head and neck cancer, renal cell cancer, clear cell renal cell cancer, breast cancer, ovarian cancer, ovarian clear cell adenocarcinoma, bone and soft tissue sarcoma (such as Ewing sarcoma, childhood rhabdomyosarcoma and uterine leiomyosarcoma), glioblastoma, gliosarcoma, nasopharyngeal cancer, uterine cancer (such as cervical cancer and endometrial cancer), anal cancer (such as anal canal cancer), colorectal cancer, hepatocellular cancer, esophageal cancer, pancreatic cancer, stomach cancer, urothelial cancer (such as bladder cancer, upper urinary tract cancer, ureteral cancer, renal pelvic cancer and urethral cancer), prostate cancer, fallopian tube cancer, primary peritoneal cancer, pleural mesothelioma and myeloproliferative syndrome. Examples of the hematologic cancer for which the Allergin-1 antagonist may be particularly effective include multiple myeloma, malignant lymphoma (such as non-Hodgkin lymphoma (such as follicular lymphoma and diffuse large B-cell lymphoma) and Hodgkin lymphoma) and leukaemia (such as acute myeloid leukaemia and chronic myeloid leukaemia).

Other than the above, the effect may also be expected in gallbladder cancer, bile duct cancer, biliary cancer, skin cancer (such as Merkel cell cancer), rectal cancer, colon cancer, testicular cancer (germ-cell cancer), vaginal cancer, vulvar cancer, penile cancer, small intestinal cancer, endocrine cancer, thyroid cancer, parathyroid cancer, adrenal cancer, brain tumor, spinal tumor, Kaposi sarcoma, squamous cell cancer, chronic or acute lymphocytic leukaemia, adult T-cell leukaemia, central nerve system primary malignant lymphoma, myelodysplastic syndrome, cancer in child and cancer of unknown primary.

The benefit of the Allergin-1 antagonist according to the present invention may be particularly recognized when it is prescribed to a cancer patient with insufficient therapeutic efficacy by an existing anti-cancer drug (antineoplastic drug). Among others, the benefit of the Allergin-1 antagonist may be particularly recognized when it is prescribed to a cancer patient with insufficient therapeutic efficacy by a tumor immunotherapeutic agent. Examples of the "cancer patient with insufficient therapeutic efficacy by an anti-cancer drug" include patients identified as "progress (PD)" by the tumor reduction effect evaluation RECIST even after a therapy with an existing anti-cancer drug. Examples of the existing anti-cancer drug include an alkylating agent, a platinum preparation, an antimetabolite (such as an antifolate, a pyridine antimetabolite, a purine antimetabolite, a ribonucleotide reductase inhibitor and a nucleotide analogue), a topoisomerase inhibitor, a microtubule polymerization inhibitor, a microtubule depolymerization inhibitor, an antibiotic antineoplastic agent, a cytokine preparation, an antihormone, a molecular targeting drug, a tumor immunotherapeutic agent and the like.

Examples of the alkylating agent include dacarbazine, nimustine, temozolomide, fotemustine, cyclophosphamide, ifosfamide and the like. Examples of the platinum preparation include cisplatin, carboplatin, oxaliplatin and the like. Examples of the antifolate include pemetrexed, leucovorin, methotrexate and the like. Examples of the pyridine antimetabolite include TS-1®, 5-fluorouracil, UFT, carmofur, doxifluridine, capecitabine and the like. Examples of the nucleotide analogue include gemcitabine and the like. Examples of the topoisomerase inhibitor include irinotecan, etoposide and the like. Examples of the microtubule polymerization inhibitor include vincristine, vinblastine, vinorelbine and the like. Examples of the microtubule depolymerization inhibitor include docetaxel, paclitaxel and the like. Examples of the antibiotic antineoplastic agent include bleomycin, mitomycin C, epirubicin and the like. Examples of the cytokine preparation include IFN-α 2a, IFN-α 2b, PEG-IFN-α 2b, natural IFN-β, interleukin-2 and the like. Examples of the antihormone include tamoxifen, fulvestrant, goserelin, leuprorelin, anastrozole, letrozole, exemestane and the like. Examples of the molecular targeting drug include imatinib, sorafenib, sunitinib, bevacizumab, gefitinib, erlotinib, crizotinib, temsirolimus, everolimus, axitinib, pazopanib, regorafenib, cetuximab, rituximab, ibrutinib, ofatumumab, panitumumab and the like.

As used herein, the term "tumor immunotherapy" or the like is a therapy for enhancing the immune reaction for cancer, namely for enhancing the immunity for cancer, thereby suppressing proliferation of cancer or reducing or eliminating cancer. The term "tumor immunotherapeutic agent" means an agent capable of enhancing the immune reaction. Examples of the therapeutic agent include an anti-PD-1 antibody (such as a human anti-human PD-1 monoclonal (neutralizing) antibody (such as Nivolumab and REGN-2810) and a humanized anti-human PD-1 monoclonal (neutralizing) antibody (such as Pembrolizumab, PDR-001, BGB-A317 and AMP-514 (also known as MEDI0680)), ANB011 (also known as TSR-042) and STI-A1110), an anti-PD-L1 antibody (such as Atezolizumab (also known as RG7446 or MPDL3280A), Avelumab (also known as PF-06834635 or MSB0010718C), Durvalumab (also known as MEDI4736), BMS-936559, STI-1010, STI-1011 and STI-1014), a PD-1 antagonist (such as AUNP-12), an anti-PD-L2 antibody, a PD-L1 fusion protein, a PD-L2 fusion protein (such as AMP-224), an anti-CTLA-4 antibody (such as Ipilimumab and Tremelimumab), an anti-LAG-3 antibody (such as BMS-986016 and LAG525), an anti-Tim3 antibody (such as MBG453), an anti-KIR antibody (such as Lirilumab), an anti-BTLA antibody, an anti-TIGIT antibody, an anti-VISTA antibody, an anti-CD137 antibody (such as Urelumab), an anti-OX40 antibody (such as MEDI6469), an anti-HVEM antibody, an anti-CD27 antibody (such as Varlilumab), an anti-GITR antibody (such as MK-4166 and TRX-518), an anti-CD28 antibody, anti-CCR4 antibody (such as Mogamulizumab), anti-CD4 antibody (such as MTRX-1011A, TRX-1, Ibalizumab, huB-F5, Zanolimumab, 4162W94, Cleno1iximab, Keliximab, AD-519, PRO-542, Cedelizumab, TNX-355, Dacetuzumab, Tregalizumab, Priliximab, MDX-CD4, CAMPATH-9 and IT1208), a TLR agonist, a STING agonist (such as MIW815) and the like. The tumor immunotherapeutic agent as used herein does not encompass the Allergin-1 antagonist according to the present invention.

Nivolumab may be produced according to the method disclosed in WO 2006/121168, Pembrolizumab may be produced according to the method disclosed in WO 2008/156712, BMS-936559 may be produced according to the method disclosed in WO 2007/005874 and Ipilimumab may be produced according to the method disclosed in WO 2001/014424.

The Allergin-1 antagonist according to the present invention is usually administered systemically or locally in a parenteral form. The dosage may vary according to the age, body weight, symptoms, therapeutic efficacy, manner of administration, treatment period and the like. However, the Allergin-1 antagonist may be usually administered in the range of 0.1 μg/kg to 300 mg/kg and particularly preferably in the range of 0.1 mg/kg to 10 mg/kg per dose per adult one to a few times a day by parenteral administration or by intravenous continuous administration over the period of 1 hour to 24 hours per day. As described above, the dosage may vary according to various conditions. Thus, a sufficient dosage may be less than the above or a higher dosage than the above range may be required.

The Allergin-1 antagonist according to the present invention may be combined with one or more other agents (mainly an anti-cancer drug) used for treatment of cancer described above in order to (1) suppress the progress of, suppress the recurrence of and/or enhance the therapeutic efficacy on cancer, (2) reduce the dosage of the other agent(s) used in combination and/or (3) alleviate the side effect of the other agent(s) used in combination. When the Allergin-1 antagonist and the other agent(s) are separately administered, the Allergin-1 antagonist may be administered prior to administration of the other agent(s), the other agent(s) may be administered prior to administration of the Allergin-1 antagonist, or there may be certain a period over which both agents are administered simultaneously. The agents may be administered by the same or different manner of administration. According to the characteristics of the agents, a preparation containing the Allergin-1 antagonist and a preparation containing the other agent(s) may be provided as a kit. The dosage of the other agent(s) may be appropriately selected on the basis of the clinically used dose. The other agent(s) may be administered by combining any two or more agents at appropriate proportions. The other agent(s) encompasses existing agents as well as agents which will be discovered in future.

Examples of the anti-cancer drug which may be mainly exemplified as the other agent(s) include the anti-cancer drug described above.

The Allergin-1 antagonist according to the present invention is formulated as an injection or infusion and used. The injection or infusion may be in any form among an aqueous solution, a suspension or an emulsion or may be formulated as a solid agent to be used by addition of a solvent before use to dissolve, suspend or emulsify the same. Examples of the solvent used for the injection or infusion include distilled water for injection, saline, dextrose solution and an isotonic solution (such as a solution of sodium chloride, potassium chloride, glycerine, mannitol, sorbitol, boric acid, borax or propylene glycol) and the like.

Examples of a pharmaceutically acceptable carrier which is used for an injection, an infusion or a solid agent to be used by addition of a solvent before use to dissolve, suspend or emulsify the same include a stabiliser, a solubilising agent, a suspending agent, an emulsifying agent, a soothing agent, a buffering agent, a preservative, an antiseptic, a pH controlling agent, an antioxidant and the like. Examples of the stabiliser which may be used include various amino acids, albumin, globulin, gelatine, mannitol, glucose, dextran, ethylene glycol, propylene glycol, polyethylene glycol, ascorbic acid, sodium hydrogen sulphite, sodium thiosulphate, sodium edetate, sodium citrate, dibutylhydroxytoluene and the like. Examples of the solubilising agent which may be used include an alcohol (such as ethanol), a polyalcohol (such as propylene glycol and polyethylene glycol), a nonionic surfactant (such as Polysorbate 80° and HCO-50) and the like. Examples of the suspending agent which may be used include glyceryl monostearate, aluminium monostearate, methylcellulose, carboxymethylcellulose, hydroxymethylcellulose, sodium lauryl sulphate and the like. Examples of the emulsifying agent which may be used include gum arabic, sodium arginate, tragacanth and the like. Examples of the soothing agent which may be used include benzyl alcohol, chlorobutanol, sorbitol and the like. Examples of the buffering agent which may be used include phosphate buffer, acetate buffer, borate buffer, carbonate buffer, citrate buffer, Tris buffer, glutamate buffer, epsilon aminocapronate buffer and the like. Examples of the preservative which may be used include methyl para-oxybenzoate, ethyl para-oxybenzoate, propyl para-oxybenzoate, butyl para-oxybenzoate, chlorobutanol, benzyl alcohol, benzalkonium chloride, sodium dehydroacetate, sodium edetate, boric acid, borax and the like. Examples of the antiseptic which may be used include benzalkonium chloride, para-oxybenzoic acid, chlorobutanol and the like. Examples of the pH controlling agent which may be used include hydrochloric acid, sodium hydroxide, phosphoric acid, acetic acid and the like. Examples of the antioxidant which may be used include (1) a water-soluble antioxidant such as ascorbic acid, cysteine hydrochloride, sodium bisulphate, sodium metabisulphite and sodium sulphite, (2) an oil-soluble antioxidant such as ascorbyl palmitate, butylated hydroxy anisole, butylated hydroxytoluene, lecithin, propyl gallate and α-tocopherol and (3) a metal chelating agent such as citric acid, ethylenediamine tetraacetic acid, sorbitol, tartaric acid and phosphoric acid.

The injection or infusion may be produced by sterilising in the final process or by an aseptic procedure such as sterilizing by filtration through a filter and packing in a sterilised container. The injection or infusion may be used by dissolving aseptic powder (which may contain powder of a pharmaceutically acceptable carrier) obtained by vacuum drying or freeze drying in an appropriate solvent before use.

The present invention is more specifically described by way of Examples hereinbelow which do not limit the scope of the invention. It should be noted that a person skilled in the art can make various changes and modifications on the basis of the description of the present invention and such changes and modifications are also encompassed by the present invention.

EXAMPLES

Example 1: Preparation of Allergin-1KO Mice

An Allergin-1 targeting vector was constructed. Specifically, the first exon including the initiation codon of Allergin-1 was substituted by a neomycin resistance gene cassette (FIG. 1A). ES cells derived from C57BL/6N mice were transfected with the linearized Allergin-1 targeting vector by electroporation. The cells were subjected to selection by the drug resistance screening and homologous recombined clones were selected by Southern blotting. With the positive clones, chimera mice were prepared by aggregation. Eight-cell stage embryos of the ICR were used as recipient embryos. The occurrence rate of chimera of the obtained chimera mice was judged based on the coat color of the whole body. The obtained individual chimera mouse was crossed with a C57BL/6N mouse and the F1 offsprings were genetically analysed by Southern blotting to obtain F1 heterozygous individuals. The male and female of the F1 heterozygous individuals were crossed and it was verified that Alg1-KO mice were obtained by genetic analysis using Southern blotting (FIG. 1B).

As the Allergin-1KO mice did not show particularly apparent phenotype, it is expected that the side effect of the Allergin-1 antagonist may be minor.

Example 2: Tumor Proliferation (MC38) in Allergin-1KO Mice

Figure 2:
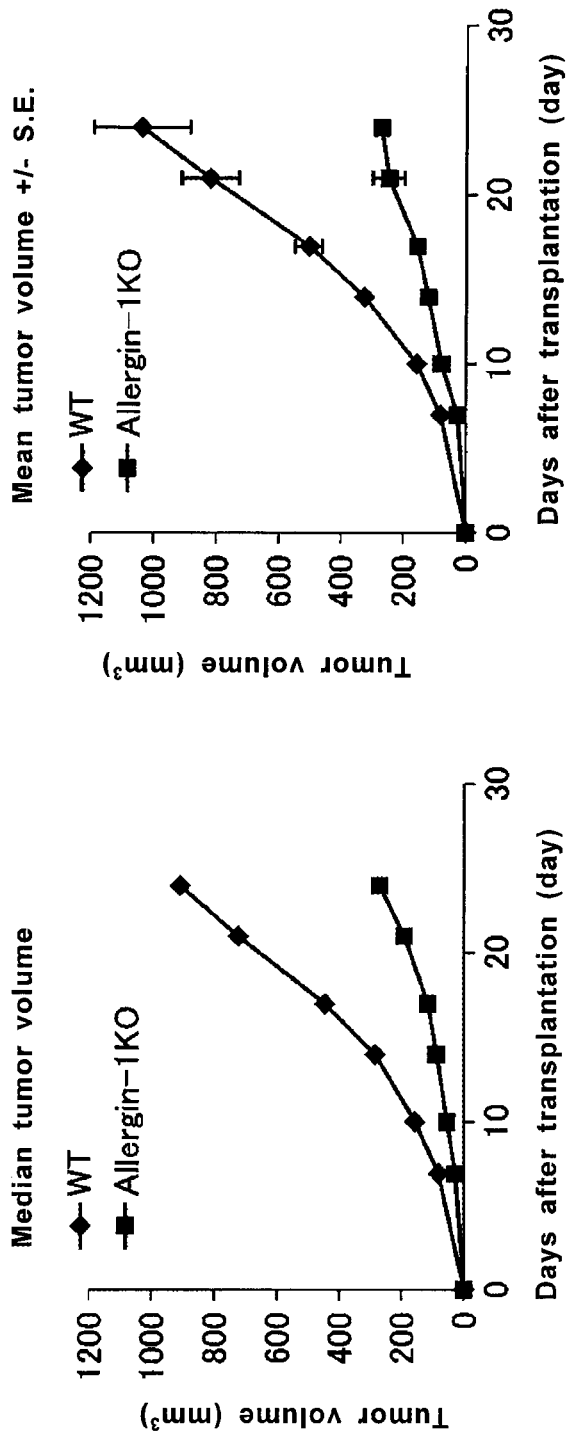
FIG. 2 shows the transition (median and mean value) of the MC38 tumor volume in C57BL/6 mice (WT mice) and Allergin-1KO mice carrying mouse colorectal cancer cell line MC38.

To C57BL/6 mice (WT mice) and Alg1-KO mice, MC38 was subcutaneously transplanted at $2.0\times10^5$/mouse. The number of mice in one group was 15. The tumor volume of MC38 was measured on day 7, 10, 14, 17, 21 and 24 after transplantation. FIG. 2 shows the transitions of the tumor volume in median (FIG. 2, left panel) and mean±standard error (FIG. 2, right panel) for each group. In the Allergin-1KO mice, tumor proliferation was significantly suppressed compared to the wild-type mice.

Example 3: Tumor Proliferation (B16F10) in Allergin-1KO Mice

Figure 3:
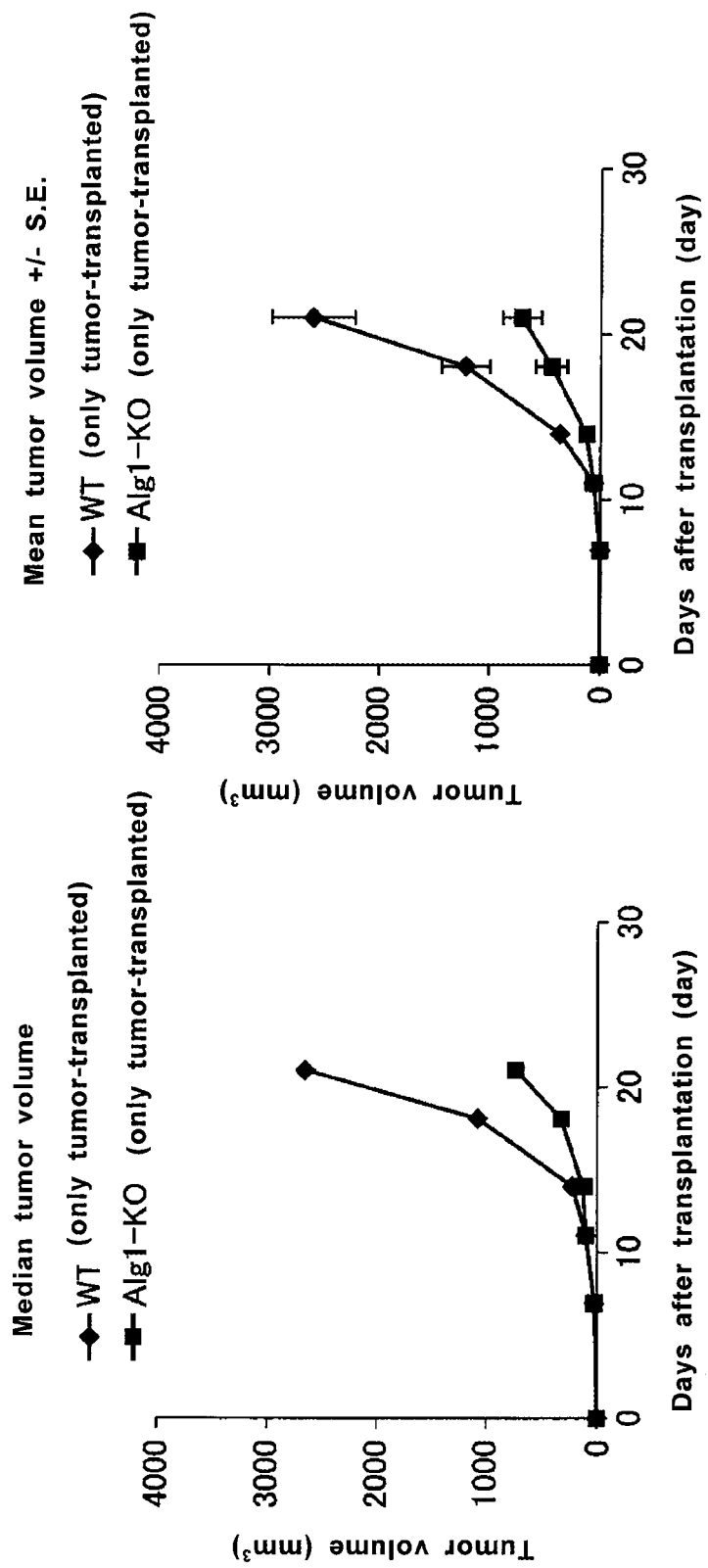
FIG. 3 shows the transition (median and mean value) of the B16F10 tumor volume in C57BL/6 mice (WT mice) and Allergin-1KO mice carrying mouse melanoma cell line B16F10.

To C57BL/6 mice (WT mice) and Alg1-KO mice, B16F10 was subcutaneously transplanted at $2.0\times10^5$/mouse. The number of mice in one group was 10. The tumor volume of B16F10 in each group was measured on day 7, 11, 14, 18 and 21, provided that the day of transplantation was day 0. In the anti-mouse PD-1 antibody 4H2 (an antibody prepared according to the method disclosed in Example 12 in WO 2006/121168) administered group, 4H2 was intraperitoneally administered to the WT mice on the day of transplantation and day 6, 12 and 18. FIG. 3 shows the transitions of the tumor volume in median (FIG. 3, left panel) and average±standard error (FIG. 3, right panel) for each group. As shown in FIG. 3, tumor proliferation of B16F10 was also significantly suppressed in the Allergin-1KO mice compared to the wild-type mice. Meanwhile, in the group of WT mice to which the anti-mouse PD-1 antibody 4H2 was administered, the median of the tumor volume on 21 days after transplantation was 1985.6 mm$^3$ (average: 2105.0±418.4 mm$^3$). The median of the tumor volume on day 21 in the group of mice carrying tumor without administration was 2661.0 mm$^3$ (average: 2622.6±377.1 mm$^3$).

From the results in Examples 2 and 3, it was demonstrated that tumor proliferation could be suppressed by inhibiting Allergin-1.

Example 4: Effect of Anti-PD-1 Antibody in Allergin-1KO Mice

Figure 4:
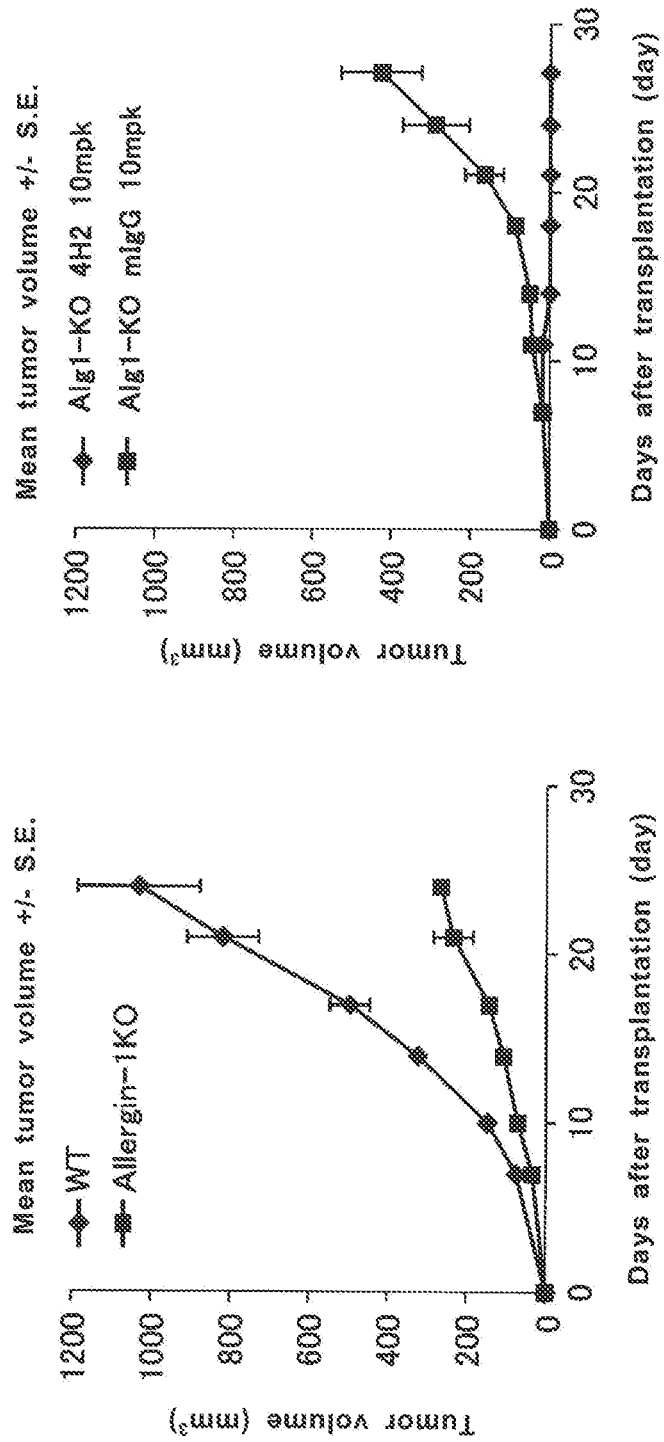
FIG. 4 shows the transition (right panel) of the MC38 tumor volume after administration of an anti-mouse PD-1 antibody 4H2 (10 mg/kg) to Allergin-1KO mice carrying MC38. In the figure, "mIgG" means a control antibody.

To C57BL/6 mice (WT mice) and Alg1-KO mice, MC38 was subcutaneously transplanted at $2.0\times10^5$ cells/mouse. The mIgG and the anti-mouse PD-1 antibody 4H2 were intraperitoneally administered on the day of transplantation and day 6 and 12, provided that the day of transplantation was day 0. The dosage of 4H2 was 10 mg/kg (20 mg/kg only on the day 0 of transplantation). The number of mice in one group was 15 for the group of mice only carrying tumor (FIG. 4, left panel) and 10 for the groups of mice to which the antibodies were administered (FIG. 4, right panel). The tumor volume of MC38 was measured on day 7, 11, 14, 18, 21, 24 and 27 after transplantation. FIG. 4 shows the transition of the tumor volume in average±standard error for each group. In the group of Allergin-1KO mice to which the 4H2 antibody was administered, tumor proliferation was further suppressed compared to the group of Allergin-1KO mice to which the control antibody was administered, namely tumor proliferation was not observed during the measurement period.

From the results in Examples 3 and 4, it was demonstrated that a synergistic effect was exhibited by Allergin-1 inhibition and PD-1 inhibition.

Example 5: Immunity Enhancement for Cancer in Allergin-1KO Mice

Figure 5:
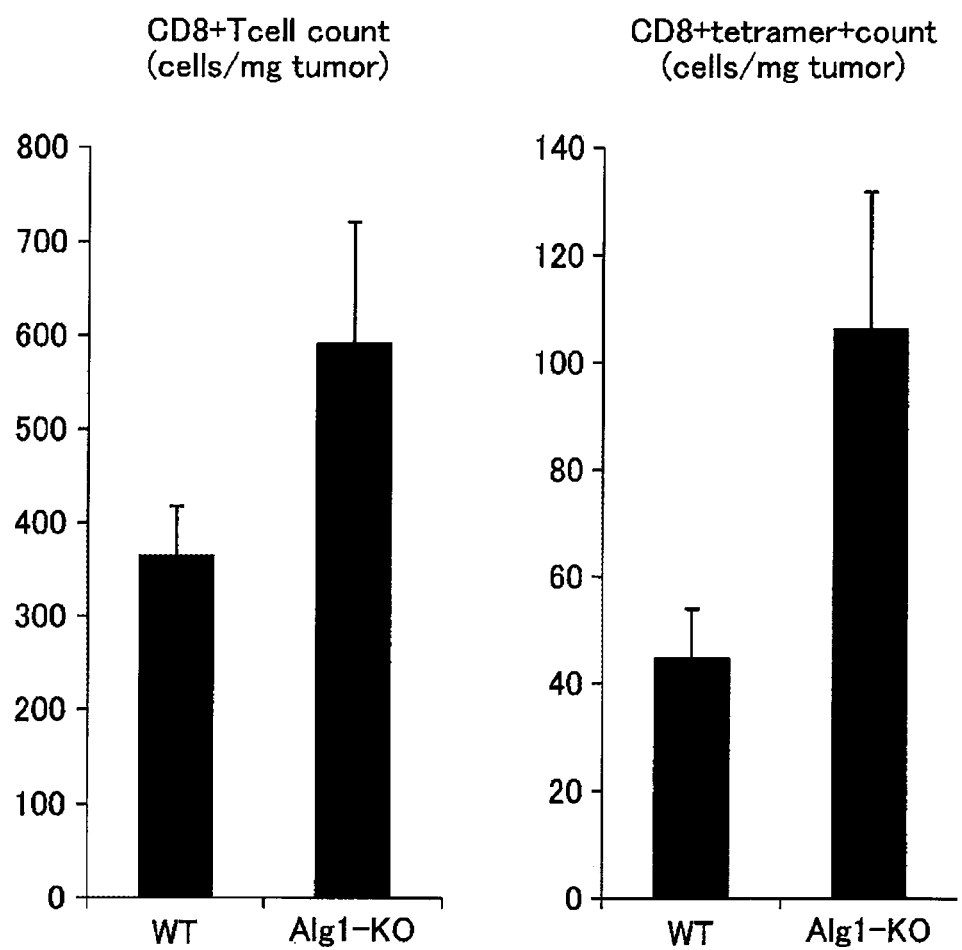
FIG. 5 shows the results of tumor-infiltrating lymphocytes analysis in C57BL/6 mice (WT mice) and Allergin-1KO mice carrying MC38.

To C57BL/6 mice (WT mice) and Alg1-KO mice, MC38 was subcutaneously transplanted at $2.0\times10^5$ cells/mouse. The number of mice in one group was 11 or 12. On 15 days after transplantation, tumor was removed from the mice and treated with collagenase to prepare tumor cells. The prepared cells were subjected to antibody staining and the number of tumor-infiltrating CD8 positive T cells and the number of tumor antigen (p15E)-specific CD8 positive T cells were measured by FACS. FIG. 5 shows the number of infiltrating lymphocytes per 1 mg of tumor in average±standard error. In the Allergin-1KO mice, the tumor-infiltrating CD8 cells ("CD8$^+$T cell" in FIG. 5) and the tumor-specific CD8 cells ("CD8$^+$tetramer$^+$" in FIG. 5) were significantly increased compared to the wild-type mice.

Example 6: Enhancement of IFNα Production in Allergin-1KO Mice

Figure 6:
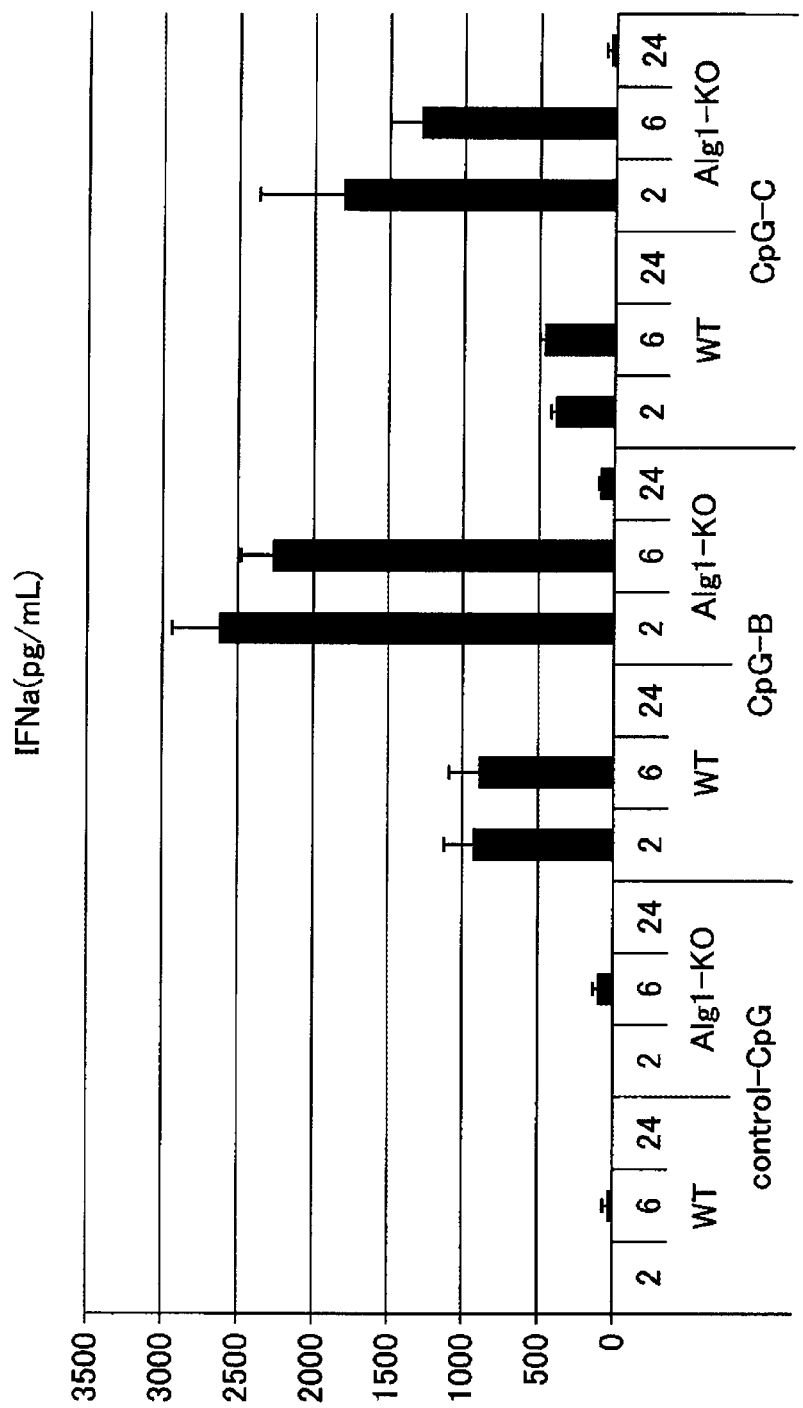
FIG. 6 shows the results of blood IFNα measurement after administration of a TLR9 agonist (CpG) to C57BL/6 mice (WT mice) and Allergin-1KO mice.

Various CpG oligonucleotides (CpG-ODNs) were mixed with a lipofection reagent DOTAP and administered to C57BL/6 mice (WT mice) and Allergin-1KO mice via the tail vein at 52 nmol/kg. At 2, 6 and 24 hours after administration, blood was collected from the tail vein and the blood IFNα was measured by ELISA. FIG. 6 shows the blood IFNα (pg/mL) in average±standard error at each evaluation point for each group. In the Allergin-1KO mice, IFNα production was significantly increased compared to the wild-type mice.

From the results in Examples 5 and 6, it was demonstrated that Allergin-1 inhibition enhanced the immunity against tumor.

Example 7: Effect of Anti-PD-1 Antibody in Allergin-1KO Mice

Figure 7:
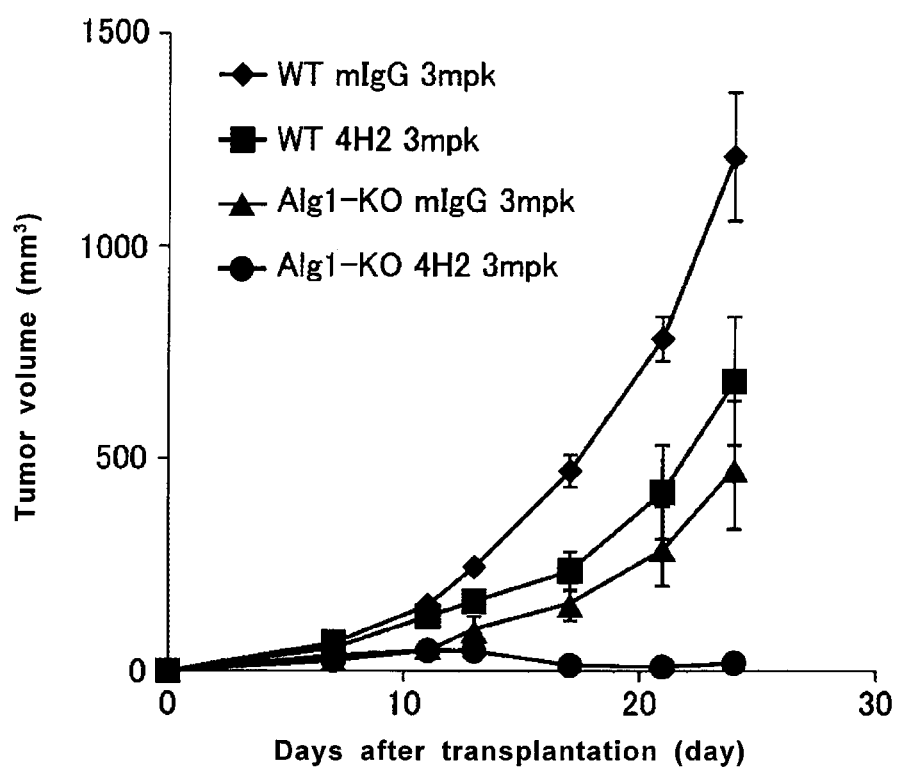
FIG. 7 shows the transition of the MC38 tumor volume after administration of an anti-mouse PD-1 antibody 4H2 (3 mg/kg) to C57BL/6 mice (WT mice) and Allergin-1KO mice carrying MC38. In the figure, "mIgG" means a control antibody.
Figure 8:
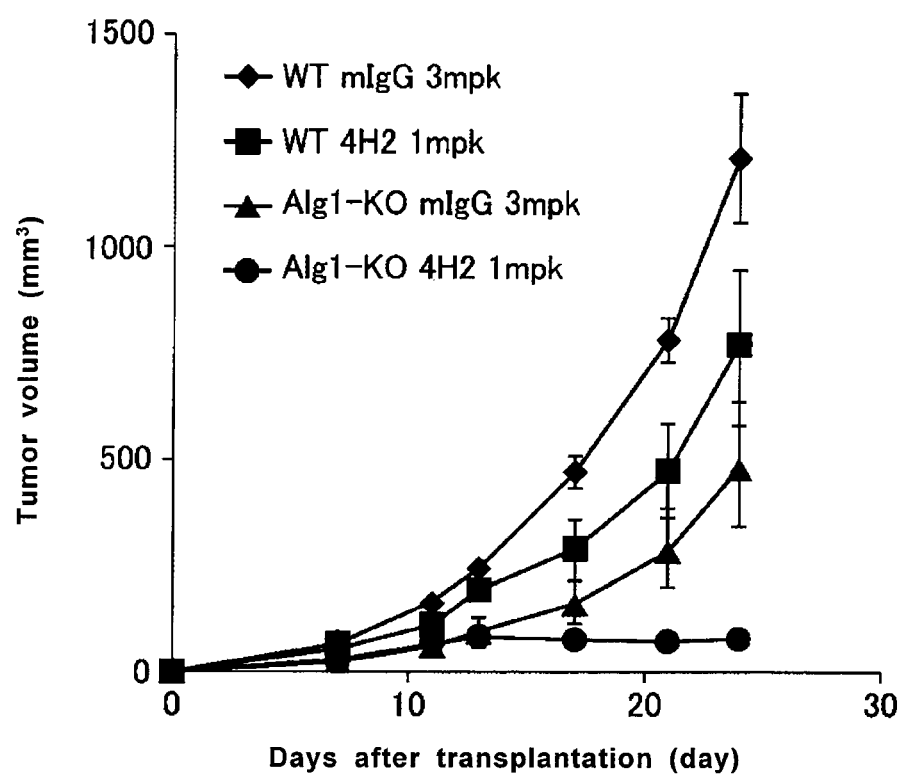
FIG. 8 shows the transition of the MC38 tumor volume after administration of an anti-mouse PD-1 antibody 4H2 (1 mg/kg) to C57BL/6 mice (WT mice) and Allergin-1KO mice carrying MC38.

To C57BL/6 mice (WT mice) and Alg1-KO mice, MC38 was subcutaneously transplanted at 2.0×10$^5$ cells/mouse. The control antibody mIgG and the anti-mouse PD-1 antibody 4H2 were intraperitoneally administered on the day of transplantation and day 6 and 12, provided that the day of transplantation was day 0. The dosage of 4H2 was 1 or 3 mg/kg. The number of mice in one group was 10. The tumor volume of MC38 was measured on day 7, 11, 13, 18, 21 and 24 after transplantation. FIGS. 7 and 8 show the profiles of the tumor volume in average±standard error for each group.

In the groups of Alg1-KO mice to which 1 and 3 mg/kg of 4H2 antibody was administered, the anti-tumor effect was observed at a similar level as that in Example 4. The number of animals in each group which showed tumor regression on day 32 is indicated below.

TABLE 1

| Mouse | Antibody (1 mg/kg) | Number of animals with tumor regression | Mouse | Antibody (3 mg/kg) | Number of animals with tumor regression |
|---|---|---|---|---|---|
| WT | 4H2 | 0/10 | WT | 4H2 | 0/10 |
| Alg1-KO | mIgG | 0/10 | Alg1-KO | mIgG | 0/10 |
| Alg1-KO | 4H2 | 5/10 | Alg1-KO | 4H2 | 9/10 |

Example 8: Effect of Anti-CD4 Antibody in Allergin-1KO Mice

Figure 9:
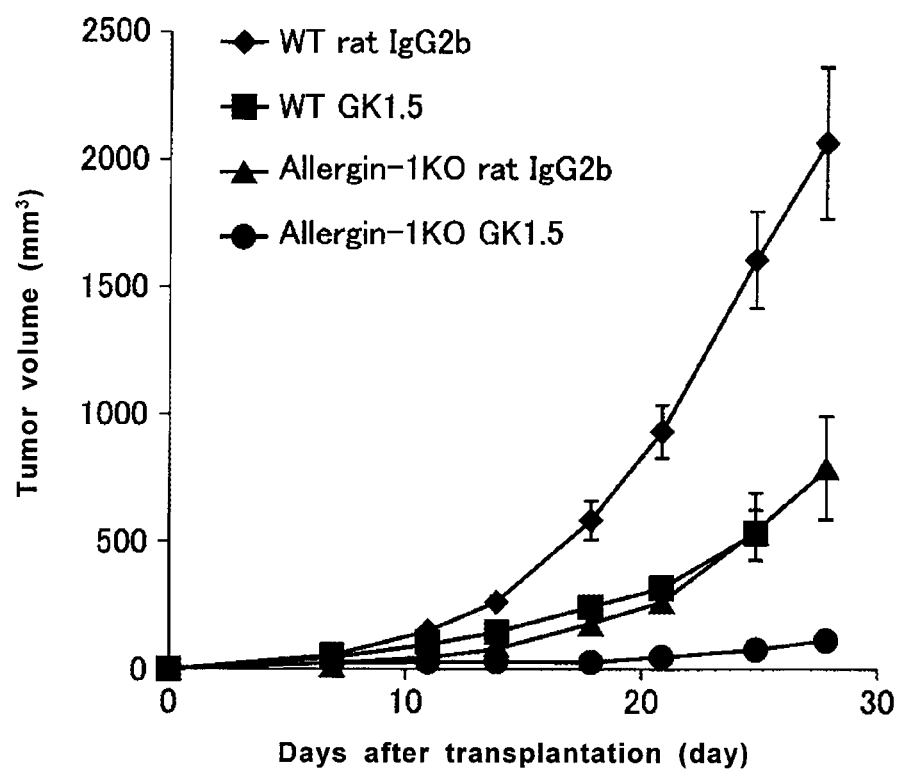
FIG. 9 shows the transition of the MC38 tumor volume after administration of an anti-mouse CD4 antibody GK1.5 (5 mg/kg) to C57BL/6 mice (WT mice) and Allergin-1KO mice carrying MC38. In the figure, "rat $IgG_{2b}$" means a control antibody.
Figure 10:
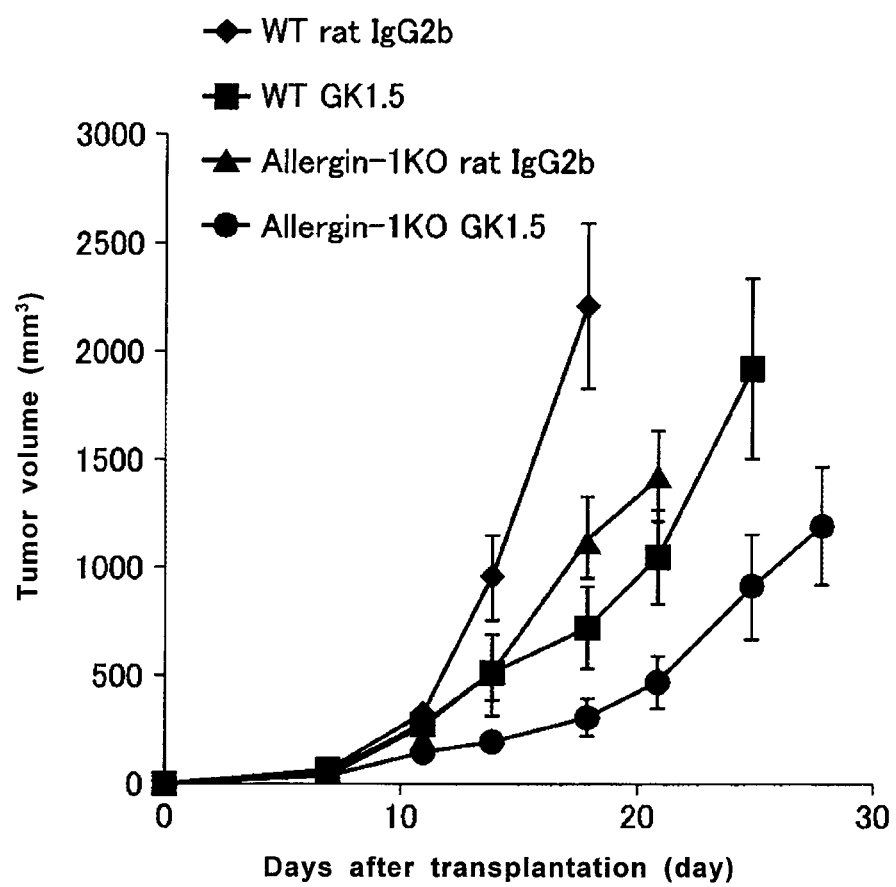
FIG. 10 shows the transition of the B16F10 tumor volume after administration of an anti-mouse CD4 antibody GK1.5 (5 mg/kg) to C57BL/6 mice (WT mice) and Allergin-1KO mice carrying B16F10.

To C57BL/6 mice (WT mice) and Alg1-KO mice, MC38 or B16F10 was subcutaneously transplanted at 2.0×10$^5$ cells/mouse. The control antibody rat IgG$_{2b}$ and the anti-mouse CD4 antibody GK1.5 (BioXcell) were intraperitoneally administered on day 5, provided that the day of transplantation was day 0. The dosage of the antibodies was 5 mg/kg. The number of mice in one group was 10. The tumor volume of MC38 and B16F10 was measured on day 7, 11, 14, 18, 21, 25 and 28 after transplantation. When a half or more animals in a group died or were euthanized, the measurement immediately after the observation thereof was the last day of the tumor measurement. FIGS. 9 and 10 show the transitions of the tumor volume in average±standard error for each group. In the group of Alg1-KO mice to which GK1.5 was administered, tumor proliferation was further suppressed compared to the group of Alg1-KO mice to which the control antibody was administered.

Figure 11:
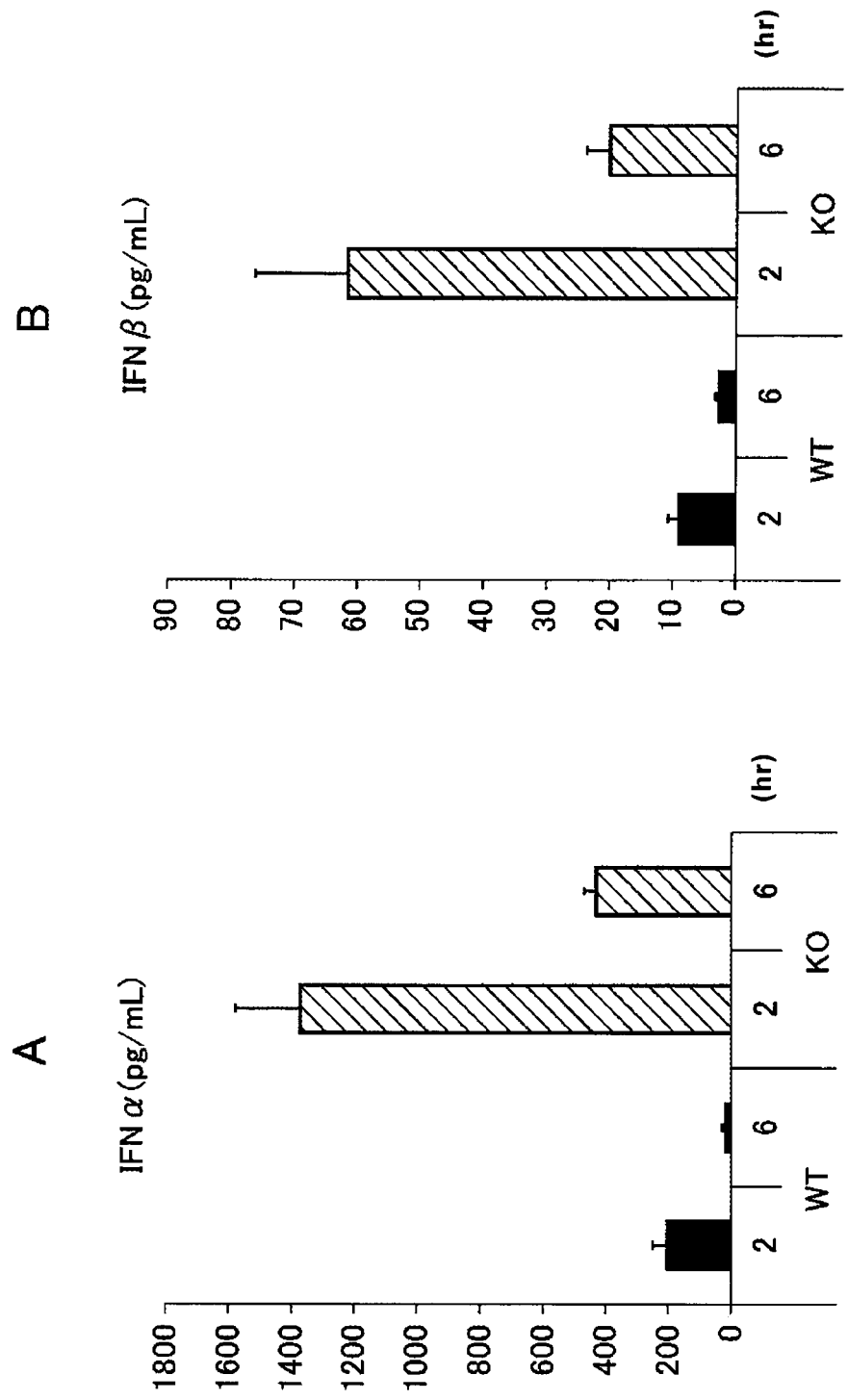
FIG. 11 shows the results of blood IFNα (in the Figure A) and IFNβ (in the Figure B) measurements after administration of a TLR7 agonist (polyuridine) to C57BL/6 mice (WT) and Allergin-1KO mice (KO).

Example 9: Production of Type I IFN in Allergin-1KO Mice after Administration of Polyuridine To C57BL/6 mice (WT mice) and Alg1-KO mice, polyuridine was intravenously administered together with a liposome transfection reagent, DOTAP. The dosage was 50 μg/mouse. Serum IFNα and IFNβ were measured by ELISA at 2 and 6 hours after administration. FIG. 11 shows serum IFNα and IFNβ for each group. In the group of Alg1-KO mice to which polyuridine was administered, production of IFNα and IFNβ was increased compared to WT.

Example 10: Production of Type I IFN after cGAMP Stimulation on Intraperitoneal Macrophages Derived from Allergin-1KO Mouse To C57BL/6N mice and Alg1-KO mice, a 3% thioglycolate medium was intraperitoneally administered at 1 mL/body. After 3 days, 5 mL of 5 mM EDTA/PBS was injected for intraperitoneal lavage and the drain was collected. After haemolysis treatment, the proportion of CD11b$^+$F4/80$^+$ cells among intraperitoneal invasive cells was calculated on a flow cytometer.

Figure 12:
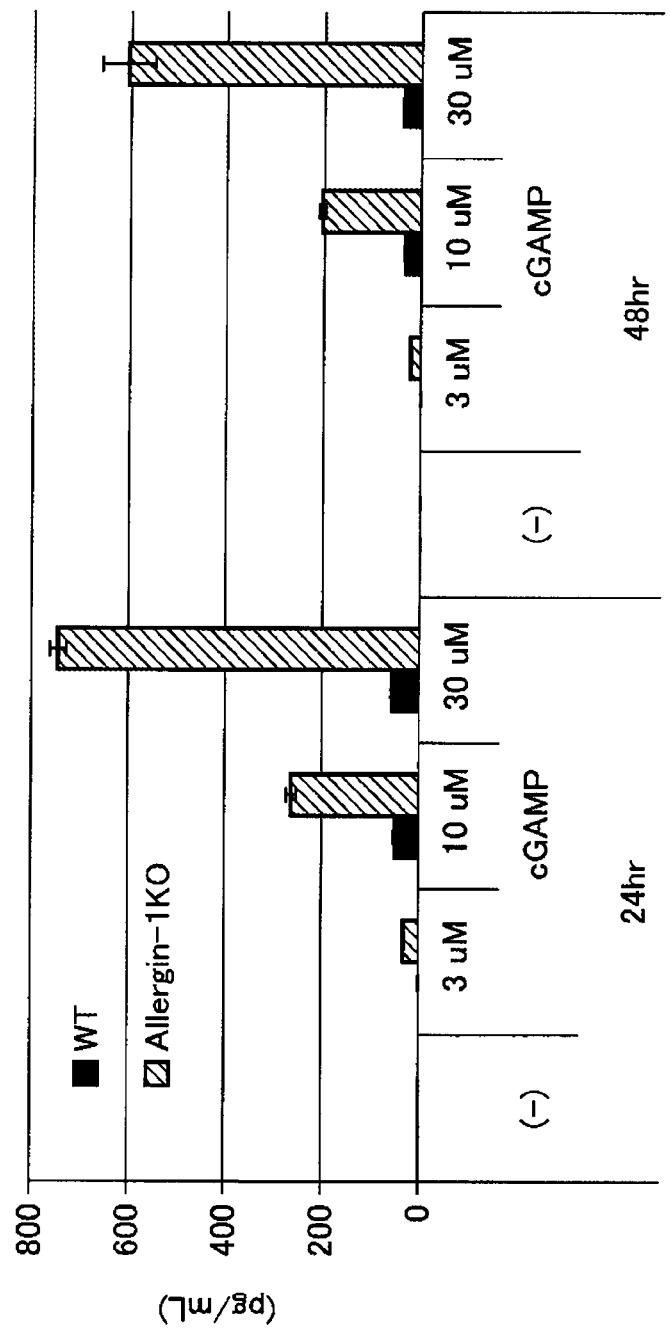
FIG. 12 shows the results of IFN measurement in culture supernatants produced after addition of a STING agonist (cGAMP) to intraperitoneal macrophages collected from C57BL/6 mice (WT) and Allergin-1KO mice.

The cells were seeded in a 96-well plate so that the CD11b$^+$F4/80$^+$ cells are 2×10$^5$ cells/well, the culture supernatant was discarded after 1 hour, the cells were washed once with the medium and the medium containing 3, 10 or 30 μM cyclic GMP-AMP (cGAMP), respectively was added. The culture supernatant was collected after 24 and 48 hours and the amount of IFN-β in the culture supernatants was measured. FIG. 12 shows the amount of IFNβ for each group. In the group of macrophages derived from Alg1-KO mice which were stimulated with cGAMP, the production of IFNβ was increased compared to WT.

Example 11: Effect of Anti-PD-1 Antibody in Allergin-1KO Mice

Figure 13:
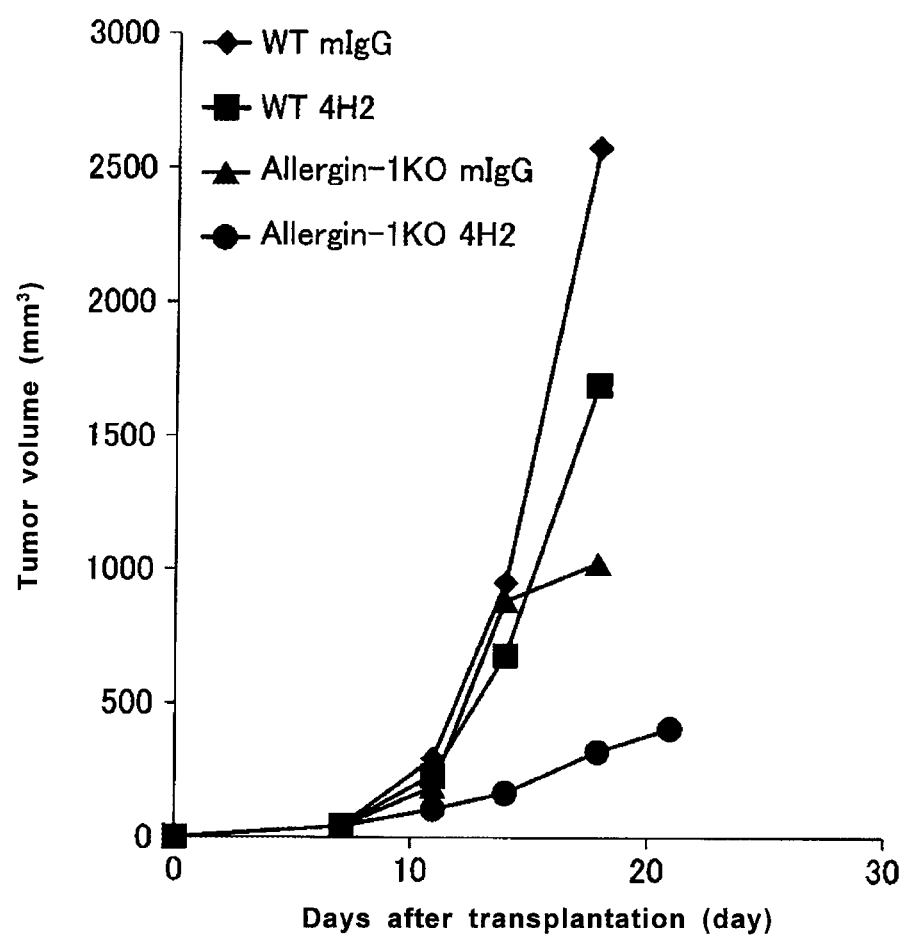
FIG. 13 shows the transition of the B16F10 tumor volume after administration of an anti-mouse PD-1 antibody 4H2 (10 mg/kg) to C57BL/6 mice (WT mice) and Allergin-1KO mice carrying B16F10.

To C57BL/6 mice (WT mice) and Alg-1KO mice, B16F10 was subcutaneously transplanted at 2.0×10$^5$ cells/mouse. The mIgG and the anti-mouse PD-1 antibody 4H2 were intraperitoneally transplanted on the day of plantation and day 6, 12 and 18, provided that the day of transplantation was day 0. The dosage of 4H2 was 10 mg/kg (20 mg/kg only on day 0 of transplantation). The number of mice in one group was 10. The tumor volume of B16F10 was measured on day 7, 11, 14, 18 and 21 after transplantation. FIG. 13 shows the transition of the tumor volume in median for each group. In the group of Allergin-1KO mice to which the 4H2 antibody was administered, tumor proliferation was significantly suppressed compared to other groups.

Example 12: Effect of Combined Use of Allergin-1 Deficiency and Anti-PD-1 Antibody in Rechallenge Test To C57BL/6 mice (WT mice) and Allergin-1KO (Alg1-KO) mice, MC38 was subcutaneously transplanted at $2.0 \times 10^5$ cells/mouse. The anti-mouse PD-1 antibody 4H2 was intraperitoneally administered on the day of transplantation and day 6, 12 and 18. The dosage of 4H2 was 10 mg/kg (20 mg/kg only on day 0 of transplantation) for WT mice and 1 mg/kg or 3 mg/kg (2 mg/kg or 6 mg/kg only on day 0 of transplantation) for Alg1-KO mice. The number of mice in one transplantation group was 20 for WT mice and 10 for each dosage of the Alg1-KO mice. On day 32 of transplantation, 8 out of 20 WT mice and 14 out of 20 Alg1-KO mice showed complete remission (CR) of tumor.

Figure 14:
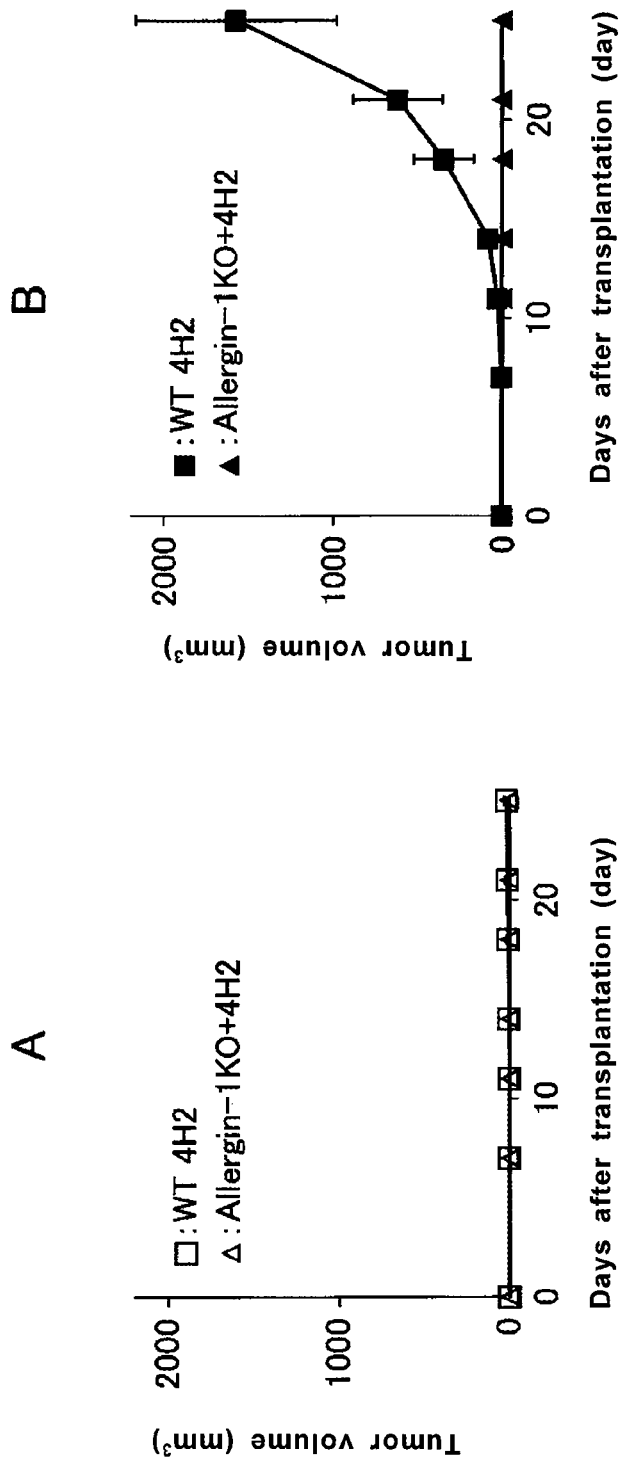
FIG. 14 shows the transition of the mean tumor volume of MC38 (A) and B16F10 (B), respectively, in C57BL/6 mice (WT mice) and Allergin-1KO mice carrying MC38 and B16F10.

To the WT mice and Alg1-KO mice which achieved CR, MC38 and B16F10 were subcutaneously transplanted on the right and left flanks, respectively, at $2.0 \times 10^5$/mouse on day 42 after the first transplantation. The tumor volume of MC38 and B16F10 was measured on day 7, 11, 14, 18, 21, 25, 28, 32, 35, 39 and 42 after transplantation. FIG. 14 shows the transition of the tumor volume in average±standard error for each group. For MC38, 7 out of 8 WT mice and all 14 Alg1-KO mice showed tumor remission. For B16F10, 1 out of 8 WT mice and 11 out of 14 Alg1-KO mice showed tumor remission, namely in the group of Alg1-KO mice which achieved CR after 4H2 administration, more CR individuals were observed than the group of WT mice which achieved CR after 4H2 administration.

This indicates that in mice from which MC38 cancer cells were completely eliminated only by PD-1 inhibition, the immunological memory was already established against MC38 cancer cells to which the immune system of the mice had been encountered, while memory CD8T cells did not sufficiently functioned against B16F10 cancer cells to which the immune system had never been encountered. Meanwhile, when PD-1 inhibition coexisted with Allergin-1 inhibition, memory CD8T cells which were established against MC38 cancer cells to which the immune system of the mice had already encountered sufficiently functioned on B16F10 cancer cells to which the immune system had never been encountered, thereby completely eliminating the same. In this context, B16F10 may be regarded as recurrent cancer cells. Namely, the results indicate that the immune system in the environment where PD-1 inhibition coexists with Allergin-1 inhibition can memorise more various cancer antigens than the cancer antigens which could be memorised by the immune system in the environment where only PD-1 inhibition exists. The spectrum of cancer antigens which are memorised by the immune system in the environment where PD-1 inhibition coexists with Allergin-1 inhibition covers cancer antigens with weak antigenicity. Therefore, it is believed that the antigens with weak antigenicity are not recognized as cancer antigens by the immune system in a normal environment and are hardly recognized as cancer antigens even in an environment only with PD-1 inhibition. Further, it is believed that if the environment with Allergin-1 inhibition is retained, cancer cells which could never be recognized by the immune system in a normal environment and could be hardly recognized in an environment only with PD-1 inhibition may be recognized as antigens and anti-tumor effect may be exhibited against new cancer cells or, in other words, recurrent cancer cells.

From the results in Examples 6, 9 and 10, it was demonstrated that Allergin-1 inhibition enhances the reactivity toward STING agonists and TLR ligands. It is believed that in an environment of Allergin-1 inhibition, the immune system recognizes cancer antigens on cancer cells having low antigenicity to activate CD8T cells and attack cancer cells, and then STING agonists and TLR ligands derived from killed cancer cells further enhance the immune reaction against cancer in an environment of Allergin-1 inhibition, thereby resulting in a synergistic effect and leading to prevention of recurrence.

INDUSTRIAL APPLICABILITY

The Allergin-1 antagonist according to the present invention is capable of enhancing the immunity for cancer and may be used for suppression of progress of, suppression of recurrence of and/or treatment of cancer.

---

The invention claimed is:

1. A method for enhancing an immunity against solid cancer,
comprising administering an Allergin-1 antagonist to a human patient with a solid cancer in an amount effective to enhance immunity against the solid cancer,
wherein the Allergin-1 antagonist is an Allergin-1-fusion protein,
wherein the Allergin-1-fusion protein is soluble in an aqueous solution and comprises a whole extracellular domain of Allergin-1 and an immunoglobulin Fc region, and is capable of inhibiting Allergin-1 signaling, and
wherein the Allergin-1, whose signaling said Allergin-1 antagonist is capable of inhibiting, and the Allergin-1, which comprises the whole extracellular domain of the Allergin-1-fusion protein, each comprises the amino acid sequence of SEQ ID NO: 1, SEQ ID NO: 2, or SEQ ID NO: 3.

2. The method according to claim 1, wherein the Allergin-1 antagonist is administered together with a pharmaceutically acceptable carrier.

3. The method according to claim 1, wherein the Allergin-1 antagonist is administered in a range of 0.1 µg/kg to 300 mg/kg per dose.

4. The method according to claim 1, wherein the Allergin-1 antagonist is administered in a range of 0.1 mg/kg to 10 mg/kg per dose.

5. The method according to claim 1, wherein the Allergin-1 antagonist suppresses progress of, suppresses recurrence of and/or treats the solid cancer.

6. The method according to claim 5, wherein the solid cancer is one or more selected from malignant melanoma, non-small cell lung cancer, small cell lung cancer, head and neck cancer, renal cell cancer, clear cell renal cell cancer, breast cancer, ovarian cancer, ovarian clear cell adenocarcinoma, bone and soft tissue sarcoma, glioblastoma, gliosarcoma, nasopharyngeal cancer, uterine cancer, anal cancer, colorectal cancer, hepatocellular cancer, esophageal cancer, pancreatic cancer, stomach cancer, urothelial cancer, prostate cancer, fallopian tube cancer, primary peritoneal cancer, pleural mesothelioma and myeloproliferative syndrome.

7. The method according to claim 1, wherein the solid cancer patient has been treated with or is treated with another therapeutic agent that is an anti-cancer drug.

8. The method according to claim 7, wherein the anti-cancer drug is one or more fusion protein or one or more antibody,
wherein the one or more fusion protein is selected from the group consisting of a PD-L1 fusion protein and a PD-L2 fusion protein, and
wherein the one or more antibody is one or more full-length antibody or one or more antibody fragment selected from the group consisting of Fab, Fab', Fv, scFv, and (Fab')₂ fragment, and
wherein the one or more antibody is selected from an anti-PD-1 antibody, an anti-PD-L1 antibody, an anti-PD-L2 antibody, an anti-CTLA-4 antibody, an anti-LAG-3 antibody, an anti-Tim3 antibody, an anti-KIR antibody, an anti-BTLA antibody, an anti-TIGIT antibody, an anti-VISTA antibody, an anti-CD137 antibody, an anti-OX40 antibody, an anti-HVEM antibody, an anti-CD27 antibody, an anti-GITR antibody, an anti-CD28 antibody, an anti-CCR4 antibody and an anti-CD4 antibody.

9. The method according to claim 8, wherein the anti-PD-1 antibody is Nivolumab or Pembrolizumab.

10. The method according to claim 8, wherein the anti-PD-L1 antibody is Atezolizumab, Avelumab, or Durvalumab.

11. The method according to claim 8, wherein the anti-CTLA-4 antibody is Ipilimumab or Tremelimumab.

12. The method according to claim 1, further comprising administering one or more anti-cancer drugs to the solid cancer patient.

13. The method according to claim 12, wherein the Allergin-1 antagonist and the anti-cancer drug are in different preparations.

14. The method according to claim 12, wherein the Allergin-1 antagonist and the anti-cancer drug are in one preparation.

15. The method according to claim 12, wherein the anti-cancer drug is one or more fusion protein or one or more antibody,
wherein the one or more fusion protein is selected from the group consisting of a PD-L1 fusion protein and a PD-L2 fusion protein, and
wherein the one or more antibody is one or more full-length antibody or one or more antibody fragment selected from the group consisting of Fab, Fab', Fv, scFv, and (Fab')₂ fragment, and
wherein the one or more antibody is selected from an anti-PD-1 antibody, an anti-PD-L1 antibody, an anti-PD-L2 antibody, an anti-CTLA-4 antibody, an anti-LAG-3 antibody, an anti-Tim3 antibody, an anti-KIR antibody, an anti-BTLA antibody, an anti-TIGIT antibody, an anti-VISTA antibody, an anti-CD137 antibody, an anti-OX40 antibody, an anti-HVEM antibody, an anti-CD27 antibody, an anti-GITR antibody, an anti-CD28 antibody, an anti-CCR4 antibody and an anti-CD4 antibody.

16. The method according to claim 15, wherein the anti-PD-1 antibody is Nivolumab or Pembrolizumab.

17. The method according to claim 15, wherein the anti-PD-L1 antibody is Atezolizumab, Avelumab or Durvalumab.

18. The method according to claim 15, wherein the anti-CTLA-4 antibody is Tremelimumab.

* * * * *

UNITED STATES PATENT AND TRADEMARK OFFICE
CERTIFICATE OF CORRECTION

PATENT NO. : 11,638,744 B2
APPLICATION NO. : 15/757452
DATED : May 2, 2023
INVENTOR(S) : Shiro Shibayama, Hiroshi Arima and Takuya Simbo It is certified that error appears in the above-identified patent and that said Letters Patent is hereby corrected as shown below:

On the Title Page

Page 2, Column 2, Item (56) OTHER PUBLICATIONS, Line 22, delete "Feb. 21.2017," and insert --Feb. 21, 2017,-- therefor;

Page 2, Column 2, Item (56) OTHER PUBLICATIONS, Line 36, delete "11201801699." and insert --11201801699V.-- therefor;

Page 2, Column 2, Item (56) OTHER PUBLICATIONS, Line 38, before "counterpart", delete "English";

Page 2, Column 2, Item (56) OTHER PUBLICATIONS, Line 41, after "Indian", delete "English";

In the Claims

In Claim 8, Column 32, Line 14, delete "anti-0X40" and insert --anti-OX40-- therefor; and In Claim 15, Column 32, Line 15, delete "anti-0X40" and insert --anti-OX40-- therefor.

Signed and Sealed this
Fifth Day of December, 2023

Katherine Kelly Vidal
*Director of the United States Patent and Trademark Office*